(12) United States Patent
Lee et al.

(10) Patent No.: US 7,354,737 B2
(45) Date of Patent: Apr. 8, 2008

(54) BIOMOLECULE TRANSDUCTION MOTIF SIM-2-BTM AND THE USE THEREOF

(75) Inventors: Sang-Kyou Lee, Seoul (KR); Seung-Kyou Lee, Daejeon (KR); Byung-Fhy Suh, Seoul (KR); Wook-Jin Chae, Seoul (KR); Jong-Bum Kim, Seoul (KR); Jong-Sun Lee, Seoul (KR); Jung-Jin Yang, Seoul (KR)

(73) Assignee: ForHumanTech Co., Ltd., Daejeon (KR)

( * ) Notice: Subject to any disclaimer, the term of this patent is extended or adjusted under 35 U.S.C. 154(b) by 0 days.

(21) Appl. No.: 10/501,964

(22) PCT Filed: Jan. 20, 2003

(86) PCT No.: PCT/KR03/00121

§ 371 (c)(1),
(2), (4) Date: May 19, 2005

(87) PCT Pub. No.: WO03/059940

PCT Pub. Date: Jul. 24, 2003

(65) Prior Publication Data

US 2005/0222386 A1  Oct. 6, 2005

(30) Foreign Application Priority Data

Jan. 19, 2002  (KR) .................... 10-2002-0003184

(51) Int. Cl.
*C07H 21/04* (2006.01)
*C12N 15/09* (2006.01)
*C07K 14/705* (2006.01)

(52) U.S. Cl. .............. 435/69.1; 435/320.1; 435/325; 435/455; 435/471; 530/350; 536/23.5

(58) Field of Classification Search .............. None
See application file for complete search history.

(56) References Cited

U.S. PATENT DOCUMENTS 5,194,596 A * 3/1993 Tischer et al. .............. 530/399
5,350,836 A * 9/1994 Kopchick et al. ........... 530/399
6,780,642 B2 * 8/2004 Narayanan .................. 435/375

FOREIGN PATENT DOCUMENTS

WO  WO 0157277 A2 * 8/2001

OTHER PUBLICATIONS

Benjamin et al., 1998, Development 125:1591-1598.*
Vukicevic et al., 1996, PNAS USA 93:9021-9026.*
Massague, 1987, Cell 49:437-8.*
Skolnick et al., 2000, Trends in Biotech. 18:34-39.*
Bork, 2000, Genome Research 10:398-400.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Pilbeam et al., 1993, Bone 14:717-720.*

* cited by examiner

*Primary Examiner*—Manjunath N. Rao
*Assistant Examiner*—Cherie M Woodward
(74) *Attorney, Agent, or Firm*—Blakely, Sokoloff, Taylor & Zafman; Stephen M. De Klerk

(57) ABSTRACT

This invention is about a novel Biomolecule Transducton Motif (BTM), Sim-2 peptide, which has a potential to transduce many biological response modifiers effectively into the cytoplasm, intracellular organelles or nucleus of prokaryotic or eukaryotic cells in vivo and in vitro, and the related technological methods using Sim-2 BTM. This Sim-2 BTM can be used for Drug Delivery System, development of new recombinant protein vaccines or DNA/RNA vaccines, gene and protein therapy, production of pharmacologically or medicinally useful proteins or pharmacomedicinal drug therapy.

6 Claims, 31 Drawing Sheets

Negative control

Sim-2(7mer)-FITC liver

β-gal  Sim-2-β-gal lung

β-gal  Sim-2-β-gal

Heart

β-gal  Sim-2-β-gal

EGFP only

Sim-2-EGFP(50nM)

M = T CELL SPECIFIC MMP CLEAVAGE SITE

Isotype control

B cell

T cell

Sim-2 only pCD8-ζ-5XGBS only

Sim-2 + pCD8-ζ-5XGBS

Isotype control

Splenocyte

T cell

Isotype control

B cell

T cell

Isotype control

B cell

T cell (a)

(b)

(a)

(b)

Recombinant insulin

Sim-2-insulin

Sim-2-insulin-PR

BIOMOLECULE TRANSDUCTION MOTIF SIM-2-BTM AND THE USE THEREOF

CROSS-REFERENCE TO OTHER APPLICATIONS

This Application is a National Phase of International Application No. PCT/KR03/00121, filed on Jan. 20, 2003, which claims priority from Korean Patent Application No. 10-2002-0003184, filed on Jan. 19, 2002.

TECHNICAL FIELD

This invention relates to Sim-2 Biomolecule Transduction Motif (BTM), a novel intracellular biomolecule transduction peptide, which delivers biologically active, functional or/and regulatory molecules in vivo and in vitro into the cytosol, organelles or nucleus of prokaryotic and eukaryotic cells, and the utilization of the same.

BACKGROUND

Generally, living cells are not permeable to macromolecules such as proteins or nucleic acids. The fact that only small-size molecules can permeate through the membrane of living cells at very low rates has restricted the researches to develop drugs to cure, prevent or diagnose diseases using macromolecules including, for example, proteins and nucleic acids. On the other hand, because most of the substances manufactured to cure, prevent or diagnose certain diseases have to be delivered into the cytosol with effective amounts, there have been several methods developed delivering those substances from the cell surface of the target cell into the cell.

Methods used to deliver macromolecules into cells include electroporation, cytosol fusion using liposomes, highly concentrated projection technique of a projectile coated with DNA on surface, calcium-phosphorous-DNA precipitation method, DEAE-dextran transfection, infection with modified viral nucleic acids, and direct microinjection into a single cell, etc. Moreover, there have been attempts to deliver macromolecules using nanoparticles in vitro and in vivo these days, but it is only in its beginning step technologically and clinically. Furthermore, these methods can deliver macromolecules to only a few of the target cells, and its efficiency is not sufficient enough to be applied clinically. Also, most of these methods cause side effects on the other cells.

In this regard, the demand for the development of a novel method of delivering biologically active macromolecules into the target cells effectively in vivo and in vitro is increasing (L. A. Sternson, Ann. N.Y. Acad. Sci., 57, 19-21 (1987)). Chemical addition of lipid peptide (P. Hoffmann et al. Immunobiol., 177, 158-170(1988)) or use of base polymers such as polylysine or polyarginine (W-C. Chen et al., Proc. Natl. Acad. Sci., USA. 75, 1872-1876(1978)) were provided. In addition, it was reported that folate of a transporter was transferred into a cell in the form of folate-conjugate. But it has not been confirmed yet that the folate was transduced into the cytosol. Also, Pseudomonas Exotoxin is known as a transporter (T. I. Prior et al., Cell. 64, 1017-1023(1991)). However, the effects of biologically active macromolecules delivered into the cytosol and their general application have not been clearly verified yet. Therefore, an effective method of transducing biologically active macromolecules into cytosol and nucleus of living cells is highly demanded.

In addition, the efficient delivery of DNA/RNA as well as macromolecules, such as proteins, into cells in vivo and in vitro is considered as to be one of the essential technique required in the field of biotechnology and applied medical science. The delivery of DNA/RNA into cells acts as a decisive factor for gene therapies, for studying the revealation of the function of a protein encoded by the gene in vivo and in vitro, and for the development of novel remedies using DNA/RNA. However, since DNA/RNA cannot permeate the cell membrane efficiently, it is very important for using genes in basic and clinical researches to improve the permeability.

For this reason, liposomes, nanomolecules, and viral vectors etc. are developed to deliver DNA and/or RNA into a cell in vitro and in vivo, and the possibilities of the use thereof were examined and investigated. However, concerning beneficial-effects and side effects, it has numerous problems to be resolved. In particular, regarding liposomes, since the side effects against cells and the cytotoxicity are very serious, their application was limited to basic researches. As for nanomolecules, though it has been receiving attentions these days, the decomposition of carrier particles in vivo, the poor efficiency of transduction and the immunological responses elicited by the molecules should be studied further and should be resolved. As for retroviruses, it has a problem in that it cannot infect undeviding cells. Adenovirus or adeno-associated virus vector also has a very limited clinical application. Furthermore, these two types of viral vectors may elicit immune responses against the other viral proteins, so its treating efficiency has many doubts. Therefore, a new way to transduce DNA/RNA into cells efficiently and less detrimentally is needed.

Meanwhile, proteins regulating physiological phenomena in vivo, are produced by bacteria, such as E. coli, as a form of recombinant protein, and have been employed in the treatment of numerous diseases. The proteins, which were synthesized in bacteria, however, were known as to be inefficient in folding structures and functions in comparison to the naturally folded proteins in vivo. Thus, there have been lots of attempts to produce proteins in yeasts, insect cells or animal cells, and to make the proteins produced in bacteria refolded using transgenic animals. However, these methods require further studies and full understanding on many molecular cell biological intermediate steps, and their transduction efficiencies are very low. And they are not cost effective.

Several PTDs (Protein Transduction Domain) have been reported as a result of this demand. Among them, Tat protein, which is a Human Immunodeficiency Virus-1 (HIV-1) viral protein, has been mostly well studied. The Tat protein was known to operate more efficiently when containing amino acids 47 to 57 (YGRKKRRQRRR), where positive charged amino acids are concentrated, than containing full-length 86 amino acid protein (Fawell S. et al. Proc. Natl. Acad. Sci. USA 91, 664-668(1994)). Other examples of PTDs are amino acids 267 to 300 of Herpes Simplex Virus type 1 protein (HSV-1) (Elliott G. et al. Cell, 88, 223-233(1997)), amino acids 339 to 355 of Antennapedia (ANTP) protein of Drosophila (Schwarze S. R. et al. Trends Pharmacol Sci. 21, 45-48(2000)), and artificial combination of positively charged amino acids. Regarding the PTDs mentioned above, we, inventors, found that they contained lysine and arginine abundantly, wherein the arginine was considered to play a great role in the transduction of biomolecule into cells. And it was supported by the published document that disclosed transduction activities of artificial peptides consisting of positively charged amino acids. (Laus R. et al. Nature Biotechnol. 18, 1269-1272 (2000)).

With regard to the transduction mechanism of macromolecules into cells when using PTDs, there are 2 (two) hypothesises. The first is that PTDs ruin the plasma membrane, and trasmit the molecules across it. The second one is that PTD uses the plasma membrane to form a new vesicle that can carry the molecules into the cells. Moreover, there are suppositions that PTD has structural features that can form new channels in the membrane (Becker-Hapak M. et al, 2001, Jul:24(3):247-256).

However, experiments with artificially combined amino acids with 12 arginines and 12 lysines suggested that the hypothesis that the existance of lysine and arginine at specific positions induced the formation of new channels might be wrong (Rothbard J B, et al, Nature Med. 200 Nov:6(11): 1253-1257). In addition, considering the facts that only the proteins, which were bound covalently or non-covalently to PTDs, were transferred through the cell membrane, the hypothesis, that PTDs ruin the plasma membrane and translocate the molecules across it, was not acceptable. Furthermore, according to our studies, PTDs represented transduction abilities both at 37° C. and at 4° C., which suggested that PTD neither made new channels nor made new vesicles.

Recently, as a new type of PTD, MTS was developed. Its amino acid sequence was synthesized based on the signal peptide of FGF (Fibroblast Growth Factor), while amino acids of the signal peptide were known to have features quite different from those of PTD amino acids as follows. (a) 3-5 numbers of arginines or lysines exist non-continuously together with serine or threonine, and there are no glutamic acid and aspartic acid, (b) one or more basic amino acids, and 6-12 numbers of hydrophobic amino acids, (c) serine, threonine, or small size hydrophobic amino acid exists abundantly, and glutamine, aspartic acid are present in small amount, (d) 10 random amino acids are present between 1 or 2 basic amino acid(s) that are gathered together. Thus, the MTS is thought to have different features in comparison to the ordinary PTDs. That is, the MTS has different amino acid combination.

In this regard, we have tried to find out a new machinery as to the PTD transduction and decisive factors to the amino acid combination consisting of PTDs, based on the discovered features of the two types of PTDs above mentioned and based on the results of our preliminary researches. The followings are two new hypothesis derived from the decisive factors and requisites for the development of a new type of PTD of the present invention: 1) considering that i) unfolded proteins are transduced more efficiently than completely folded ones, and that ii) once the unfolded proteins are transmitted into organelles or cells they are not eliminated from the organelles or cells, and that iii) PTDs do not utilize receptors to perform endocytosis or phagocytosis, it seems that the PTDs use channels present on the cell surface. Accordingly, hydrophobic amino acids, such as alanine and valine, are highly demanded; 2) Since PTDs transmit molecules into the nucleus efficiently, its function may be similar to transcription factors. Therefore, PTDs would be found frequently in transcription factors. And the PTDs may use channels similar to translocons that transmit proteins into organelles.

Based on these two hypothesis and requisites, we searched the gene bank. With the factor that the conventional PTDs have lysines and arginines abundantly, we selected about 10,000 primary candidate genes. Among them, 500 genes were chosen by applying the requisites of signal peptide, and 100 genes of the 500 genes were confirmed as to have alanine and valine. Finally, 20 genes were selected by applying the factors required for the transcription factors, and then the transduction efficiencies were tested therefor. In addition, fusion proteins of each of these candidate PTDs and β-galactosidase were expressed and purified, and the functions of these proteins were detected using Jurkat T cells. As a consequence, amino acid sequence 558 to 566 of Sim-2 (number of gene bank: U80456), a human transcription factor, was found to have unexpectedly significant transduction ability and was named Sim-2 BTM (Biomolecule Transduction Motif).

Thus, we completed the present invention with the findings that amino acids 558 to 566 of Sim-2 have significantly excellent features as an intracellular biomolecule transduction peptide, thereby any target proteins, nucleic acids, lipids, carbohydrates and chemical compounds can be efficiently delivered into cytosol and nucleus in vivo and in vitro. Furthermore, we verified that the desired macromolecules could be transduced into specific organs and/or cells in vivo and in vitro, by employing ecto domain of the ligand, which binds to the receptor present on the surface of the cells or the organs to which the macromolecules are transduced, MMP cleavage site and Sim-2 BTM. Furthermore, we found that expression vector having 5 (five) successive DNA/RNA sequences, which specifically bind to DNA/RNA binding domains, could be transduced in vivo and in vitro into the specific organs or cells, using the Sim-2 BTM and using the DNA/RNA binding domains (DBD and/or RBD) that bind to the DNA/RNA to be transduced, wherein the expression vector could include regulatory elements comprising a promoter that induces gene expression selectively in specific organs, tissues or cells. Furthermore, according to the present invention, it is possible to reform the structure of recombinant protein to have the same folding structure and functions as those found naturally, by transferring the proteins synthesized in bacteria to the suitable animal cells and isolating them.

DETAILED DESCRIPTIONS OF THE INVENTION

The object of this invention is to provide a novel biomolecule transduction motif Sim-2-BTM (SEQ.ID No.:1), which effectively transduce biologically active, functional regulatory macromolecules in vivo and in vitro via numerous administration routes including intramascular, intraperitoneal, intravein, oral, nasal, subcutaneous, intradermal, mucosal, and inhalation routes and to provide the recombinant expression vector including it.

Another object of this invention is to provide recombinant expression vector comprising Sim-2-BTM and to provide transformed cells using the vector.

Another object of this invention is to provide the fusion protein of biomolecule transduction motif and a desired protein by transforming a suitable host cell with the recombinant expression vector.

Another object of this invention is to provide a method of transducing biologically active functional modulatory macromolecule in vivo and in vitro into the cytosol or nucleus of prokaryotes or eukaryotes using Sim-2-BTM.

Another object of this invention is to use the Sim-2 BTM in gene therapies and in disease treatment using proteins.

Another object of this invention is to provide a recombinant vaccine including Sim-2 BTM and a DNA/RNA vaccine, or delivering genes for gene therapies using Sim-2-BTM.

Another object of this invention is to provide a novel vaccine using DNA/RNA or protein antigens specific to pathogens, such as viruses, bacteria, mold, and various cancer cells.

Another object of this invention is to provide a genetic medicine of DNA/RNA, which regulates biological activities in vivo and in vitro, using Sim-2-BTM.

Another object of this invention is to provide protein drugs for the treatment, diagnosis and/or prevention of disease, wherein the folding structures of proteins are reformed to have the same structure and functions as those of proteins generated naturally.

In order to achieve these objects, this invention provides a peptide or its active fragment comprising amino acid sequence (SEQ. ID No.:1) to transduce biologically active functional modulatory macromolecules in vivo and in vitro into the cytosol or nucleus of prokaryotes or eukaryotes.

Furthermore, this invention provides a peptide or its active fragment comprising amino acid sequence (SEQ. ID No.:1) to transduce biologically active functional modulatory macromolecules in vivo and in vitro into the cytosol or nucleus of prokaryotes or eukaryotes, wherein a part of the amino acids is deleted or substituted, or at least a part of the amino acids is replaced by L- or D-form amino acids, or the structure of amino acid are reformed to enhance stability in vivo.

Furthermore, this invention provides DNA encoding intracellular biomolecule transduction peptide, recombinant DNA expression vector comprising DNAs encoding target protein, and transformed *E. coli* of DH5a Sim-2 (KCCM 10346) using the vector.

Furthermore, this invention provides a method of transducing a complex of the peptide (or the peptide fused with a target protein) and biologically active functional regulatory molecule (for example, chemical drug or chemical prodrug) via numerous administration routes includinding intramuscular, intraperitoneal, intravenous, oral, nasal, subcutaneous, intradermal, mucosal and inhalation routes, in vivo and in vitro into the cytosol or nucleus of prokaryotes or eukaryotes. The following describes this invention in detail.

In this specification and claims, "biologically active functional regulatory molecule" means the molecule, which regulates any physiological phenomenon, including, for example, DNA, RNA, protein, lipids, carbohydrates, and chemical compounds.

In addition, "an active fragment" is defined as some parts of amino acids of SEQ. ID No.:1 or its modified one in which a part of the amino acids is deleted or substituted, or at least a part of the amino acids is replaced by L- or D-form amino acids, or the structure of amino acids is reformed to enhance stability in vivo, wherein the fragment maintains intracellular biomolecule transduction activites.

In addition, "macromolecule" is defined as to include proteins, lipids, nucleic acids, carbohydrates and chemical compounds.

In addition, a biomolecule transduction peptide of "Sim-2-BTM derivative" is defined as a peptide or its active fragment, which maintains transduction activites of Sim-2-BTM, wherein a part of the amino acids is deleted or substituted, or at least a part of the amino acids is replaced by L- or D-form amino acids, or the structure of amino acids is reformed to enhance stability in vivo and in vitro.

In addition, a "fusion protein" is defined as a protein fused with biomolecule transduction peptide of Sim-2-BTM directly through chemical, physical, covalent or non-covalent bond, or indirectly through any mediator.

In addition, a "chemical compound" is defined as a chemical substance, which regulates cell's function, such as anticancer drug, immunological disease drug, antiviral drug and growth, development or differentiation factor of an animal.

In this invention, a biomolecule transduction peptide is defined as a peptide corresponding to amino acids from $558^{th}$ to $566^{th}$ from N-terminus of human transcription inhibitor Sim-2 (M. J Alkema et al., Genes Dev. 12), 226-240 (1997)), wherein arginines and alanines are considered as to interact with biomolecule transducing channel receptors on the cell surface.

In addition, this invention relates to a peptide corresponding to the amino acid sequence of SEQ. ID No.:1, wherein a portion of amino acid including arginine, lysine and alanine is substituted with functionally and structurally similar amino acids, for example, valine, etc.

This invention also provides an expression vector comprising: i) DNA/RNA encoding a biomolecule transduction peptide corresponding to amino acid sequence of SEQ. ID No.:1, or DNA/RNA encoding a biomolecule transduction peptide corresponding to modified amino acid sequence of SEQ. ID No.:1 in which a part of the amino acids is deleted or substituted or at least a part of the amino acids is replaced by L- or D-form amino acids, or DNA/RNA encoding an active fragment of the peptide; and DNA/RNA encoding a desired protein and/or biologically active functional regulatory molecules to be introduced into cells. This recombinant expression vector preferably includes tag sequence(s), such as a series of Histidine, Hemaglutinin, Myc, or Maltose binding protein codon, and so forth, in order to make the purification easier. Furthermore, in order to increase solubility, a fusion partner, such as lysine RNA polymerase, can be introduced to the vector. Furthermore, for the flexibility of the protein encoded by the genes and for the stability of the fusion protein, one or more glycine and spacer amino acids including AYY amino acids can be incorporated. Furthermore, a cleavage site recognized by a protease specifically present in a certain intracellular organelle to remove unwanted part of the fusion protein or to separate BTM and the cargo molecule, expression regulatory sequence and a marker to monitor the transduction or a reporter gene can be inserted to the expression vector, wherein the expression regulatory sequence consists of regulatory domain comprising a promoter or enhancer that is specific to cells, tissues or organs to which the desired DNA/RNA is transduced.

In one embodiment, recombinant expression vector including intracellular biomolecule transduction peptide of pSim-2-β-gal comprises DNAs encoding a peptide corresponding to amino acid sequence of SEQ. ID No.:1, 6 (six) succesive histidine codons to purify the desired proteins expressed in host cells, Asp-Asp-Asp-Asp-Lys sequence to be cleaved with enterokinase or Glu-Asn-Leu-Tyr-Phe-Gln-Gly sequence to be cleaved with Tev and DNAs encoding a marker of β-galactosidase for the detection of the desired protein in cells.

The pSim-2-β-gal vector of this invention can easily be obtained with ordinary PCR (polymerase chain reaction) methods using pIND/lacZ vector (can be obtained from Invitrogen Inc.) as a template. Also, in this invention, biomolecule transducing recombinant expression vector is manufactured by cutting out β-galactosidase gene with suitable restriction enzyme and replacing it with the desired protein coding DNAs. The desired protein comprises biologically active functional regulatory protein or its fused one, which is chemically or physically bound to ecto domain of ligand that binds specifically to a receptor of cell, tissue or organ to which the desired protein is introduced, in order to transduce it to specific cell or tissue or organ. This ligand or receptor includes protein, lipid, carbohydrate, chemical compound or its complex, but is not limited thereto. If the desired protein is any one of viral specific protein selected from a group consisting of HIV, HBV, HCV and influenza, or a tumor specific protein expressed in tumor cells including liver cancer or stomach cancer cells, the recombinant expression vector of this invention induces CTL (cytotoxic leukocyte) by converting antigen processing pathway from MHC class II to MHC class I. In this case, the recombinant expression vector preferably comprises DNAs encoding one or more ubiquitins.

In one embodiment of the present invention, the desired protein is isolated and purified using the recombinant expression vector. Specifically, after transforming a suitable host cell, such as E. coli, with the recombinant expression vector of this invention, the desired protein is isolated using interaction between polyhistidine and $Ni^{2+}$-NTA. Furthermore, in another embodiment, a method for transducing functional regulatory molecules are transduced more effectively into cytosol, organelle or nucleus by culturing the recombinant expression vector of the present invention together with biologically active functional regulatory molecules.

In another embodiment, a method of transducing biomolecules is provided as follows: i) providing recombinant expression vector comprising DNAs encoding DNA/RNA binding protein that binds selectively to DBS/RBS (DNA/RNA binding sequence) of the desired DNA/RNA; ii) obtaining protein-DNA/RNA complex by combining the desired DNA/RNA sequence, which contains target DNA/RNA sequence that binds to the DNA/RNA binding protein; and iii) mixed culturing the protein-DNA/RNA complex with cell culture medium in order to transduce the desired DNA/RNA into the cells.

In another embodiment, a method of tranasducing biomolecule is provided, which comprises: i) obtaining a complex by reacting fusion proteins, which are activated by binding inducer, with the desired chemical compound, wherein the fusion protein is a fused one between the biomolecule transduction peptide of Sim-2BTM or its derivatives and the desired protein; and ii) mixed culturing the obtained complex together with cell culture medium in order to transduce the desired chemical compounds into the cells. The binding inducers introduced above include binding reagents, for example, BMOE (Pierce Cat. No 2323), DSP (Pierce Cat. No 22585), that bind the biomolecule transduction peptide or the fusion protein between the transduction peptide and the desired protein to DNA/RNA, carbohydrate, lipid, protein or chemical compounds through chemical, physical, covalent or no-covalent bond, directly or indirectly.

In another embodiment, a method for producing a protein drug is provided as follows: i) isolating and purifying a fusion protein between biomolecule transduction peptide of Sim-2 BTM or its derivatives and the desired protein that controls biological response in vivo, after massively expressing them from bacteria; ii) and transferring the fusion protein into the cells, which produce the desired protein in natural state, or in the cells, which carry out protein processing and modification, in order to refold the protein to have natural folding structure and functions.

In addition, in this invention, when transducing the desired DNA/RNA, or chemical compound into cells, they are combined with the fusion protein between the biomolecule transducing peptide and the desired protein, wherein the desired protein can form a transduction complex by binding the ecto domain of a ligand, which selectively interacts with a receptor that is expressed in specific cells, organs and tissues, or mAb or its mutant, which binds specifically to the ligand or the receptor, for example, a Fab fragment, a F(ab') fragment, or a single strand Fv or hummanized mAb.

Thus, this invention also provides a method of transducing a desired DNA/RNA into cells as follows: i) preparing $1^{st}$ recombinant expression vector comprising a desired DNA/RNA to be transduced into cells, at least one continuous DNA/RNA sequence to which DNA/RNA binding protein binds specifically, and operably linked expression regulatory sequence; ii) preparing $2^{nd}$ recombinant expression vector comprising a peptide of SEQ. ID No.:1 or its active fragment, DNA/RNA encoding DNA/RNA binding protein that bind selectively to the DNA/RNA sequence in the $1^{st}$ recombinant expression vector of the step i); iii) collecting expressed fission protein from host cells using the $2^{nd}$ recombinant expression vector; iv) obtaining a complex of the fusion protein and the desired DNA/RNA by binding the fusion protein of iii) and $1^{st}$ recombinant expression vector of i); v) mixing the complex with the cells, to which the desired DNA/RNA is transferred, and mixed culturing the cells. As a biologically active functional regulatory factor, cytokine such as interleukin-4, interleukin-2, interleukin-12 or γ-interferon, chemokines or EGF can be employed in this invention.

The desired protein of this invention is preferably subject to post-translational modification, for example, ubiquitination, phosphorylation, fatty acylation such as palmistoilation, myristoylation or farnesylation, after translation thereof. In particular, a part of Lck protein amino acid sequence (Met-Gly-Cys-Val-Cys-Ser-Ser-Asn-Pro-Glu-Asp-Asp-Trp-Met-Glu-Asn) can be employed during the acylation process.

Furthermore, when transducing a biological active functional regulatory molecule into cytosol, organelle or nucleus of a cell, it is preferable to use lysosomotrophic agent selected from a group consisting of choroquine, monensin, amantadine, and methylamine in order to enhance the structural and functional safety of the molecule. The biological active functional regulatory molecule is transduced into cytosol, organelle or nucleus of a cell via numerous administration routes, such as intramascular, intraperitoneal, intravein, oral, nasal, subcutaneous, intradermal, mucosal, and inhalation routes, together with the Sim-2 BTM.

Since the biomolecule transducing peptide of the present invention is very small, biological intervention to the active molecule is significantly minimized.

BRIEF DESCRIPTION OF FIGURES

Below are more detailed descriptions according to practical examples. Below practical examples are there to show examples, and this invention is not limited to this range. Moreover, the technical reference of this invention is combined to the invention as a reference.

EXAMPLE

Example 1

Preparation of Expression Vector Including Sim-2-BTM of Biomolecule Transduction Peptide Nucleic acid sequence encoding peptide corresponding to amino acids from 558th of Alanine to 566th of Arginine from N-terminus human transcription factor of Sim-2 (GenBank Code: U80456) was combined with nucleic acid sequence encoding reporter protein of β-galactosidase. In order to do this, firstly, a primer of SEQ.ID No.:2 containing nucleic acid sequence encoding peptide corresponding to amino acids from 558th of Alanine to 566th of Arginine from N-terminus of Sim-2 and BamHI site for cloning, and a primer of SEQ. ID No.:3 containing nucleic acid sequence of 3' terminus of β-galactosidase and restriction enzyme of Bgl II site for cloning were derived. Then, PCR was carried out using pIND/lacZ vector (Invitrogen corp.), as a template, with pfu turbo DNA polymerase (Stratagene, cat.# 600252-51). After digesting the PCR products with restriction enzymes of BamHI and Bgl II, the results were purified with PCR purification kit (Quiaquick) (QIAGEN, cat.# 28104). The purified products were cloned to pTrcHis B (Invitrogen, Cat.No. V360-20B), which was purified with gel extraction, at Bgl II recognition site, thereby recombinant expression vector was generated and named pSim-2-β-gal. FIG. 1A illustrates the construct of the expression vector of pSim-2-β-gal. The expression vector of p Sim-2-β-gal was treated with Xba I and HindIII and then, it was subject to electrophoresis on 1% agarose gel followed by staining with ethydium bromide (see FIG. 1B). In FIG. 1B, the first column represents the present p Sim-2-β-gal, and the second column represents standard sized DNA fragments.

Example 2

Preparation of *E. coli* Transformant, and Expression and Isolation of Fusion Protein Therefrom DH5α (ATCC No. 53863) was transformed using pSim-2-β-gal of the Example 1 by heat shock transformation. 2 ml of the transformants were transferred to 100 ml of LB medium, and pre-incubated for 12 hrs at 37° C. with agitation. Then, the pre-incubated transformants were inoculated to 1000 ml of LB medium (10 g of pancreatic digests of casein, 5 g of yeast extract, 10 g of sodium chloride) and were incubated for 4 hrs at 37° C. Following the incubation, 1 mM of IPTG (Isopropyl β-D-thiogalactosipyranoside, GibcoBRL cat.# 15529-019) was added in order to induce the expression of lac operon, and then incubated again for 8 hrs to elicit expression of the fusion protein. Next, the cell culture solution was centrifuged at 6,000 rpm for 20 min at 4° C. After removing the supernatant, resultant pellet was dissolved in 10 ml of buffer solution 1 (50 mM of $NaH_2PO_4$, 300 mM of NaCl, 10 mM of Imidazole, at pH 8.0) including 1 mg/ml of lysozyme (Sigma, cat.# L-7651), and was placed on ice for 30 min. Subsequently, ultrasonification (Heat systems, ultrasonic processor XL, with 300 w) for 10 sec and freezing for 10 sec were applied to the solution, repeatedly, until the cumulative time of ultrasonification is 3 min. The eluted solution was centrifuged again at 12,000 rpm for 20 min at 4° C. so as to remove the debris of *E. coli* and isolate pure eluted solution. Then, 2.5 ml of 50% Ni$^{2+}$-NTA agarose slurry (Qiagen, cat# 30230) was added to the isolated solution, and the mixture was stirred at 200 rpm for 1 hr at 4° C. in order to bind fusion protein and Ni$^{2+}$-NTA agarose. The obtained mixture was spilt into a column (0.8×4 cm) for chromatography (BioRad, cat.# 731-1550). And the mixture was washed twice with 4 ml of buffer solution 2 (50 mM of NaH$_2$PO$_4$, 300 mM of NaCl, 20 mM of Imidazole, at pH 8.0). Thereafter, the mixture solution was treated four times with 0.5 ml of buffer solution 3 (50 mM of NaH$_2$PO$_4$, 300 mM of NaCl, 250 mM of Imidazole, at pH 8.0) to obtain fusion protein fractions. The isolated and purified Sim-2-β-gal fusion protein was subject to SDS-PAGE followed by coomassie blue staining (see FIG. 2). In FIG. 2, the first column corresponds to protein marker for use as a molecular weight standard, and the second column represents fusion protein of Sim-2-β-gal.

Example 3

Transduction of Fusion Protein Across Cell Membrane

Figure 1A:
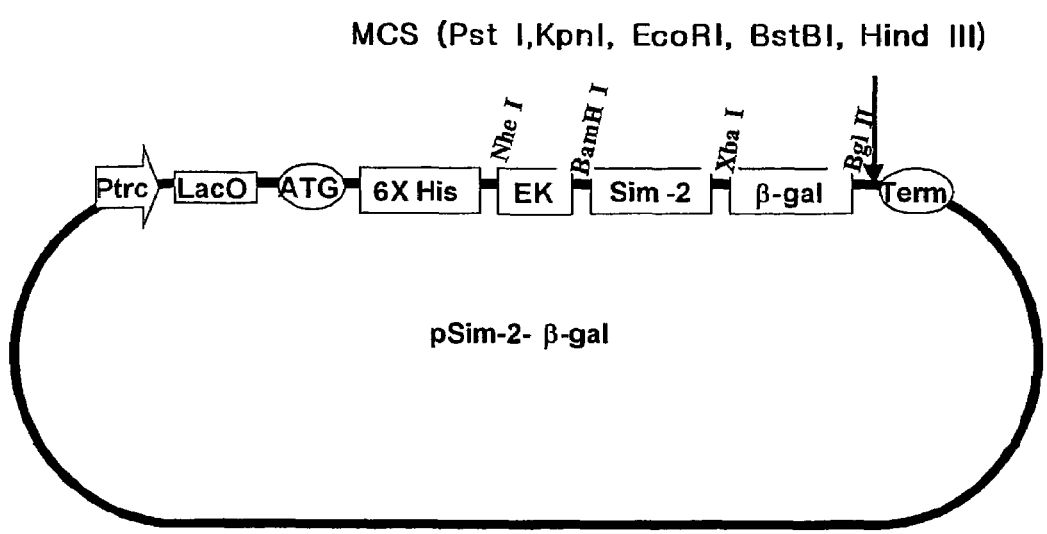
FIG. 1A illustrates the construct of expression vector pSim-2-β-gal.
Figure 1B:
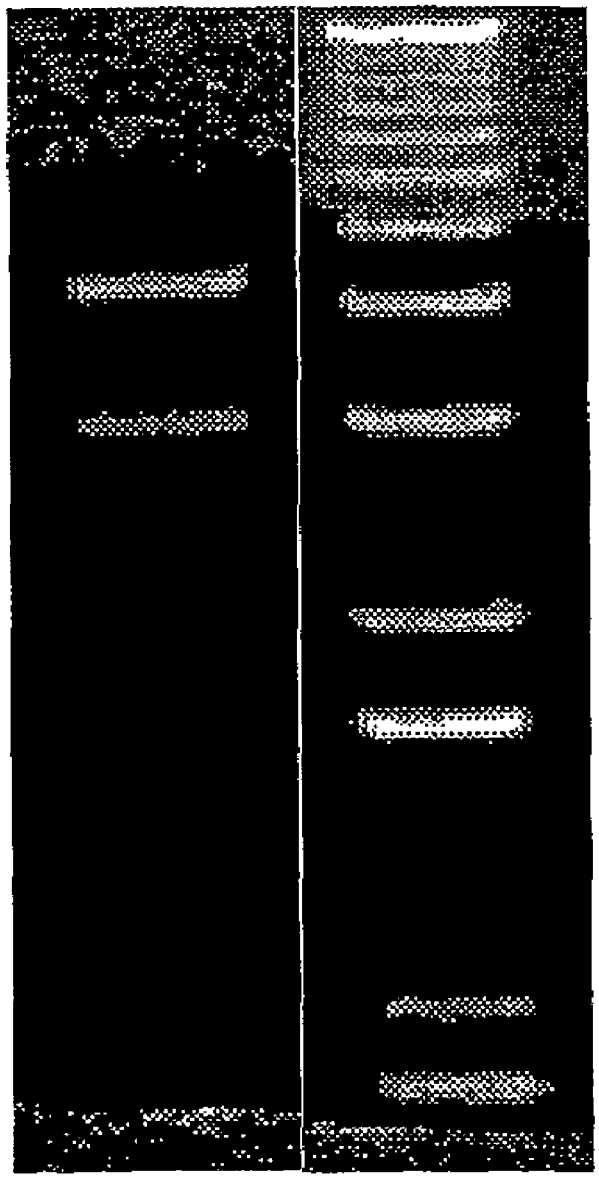
FIG. 1B shows agarose gel images after treating the vector of FIG. 1A with restriction enzymes.
Figure 2:
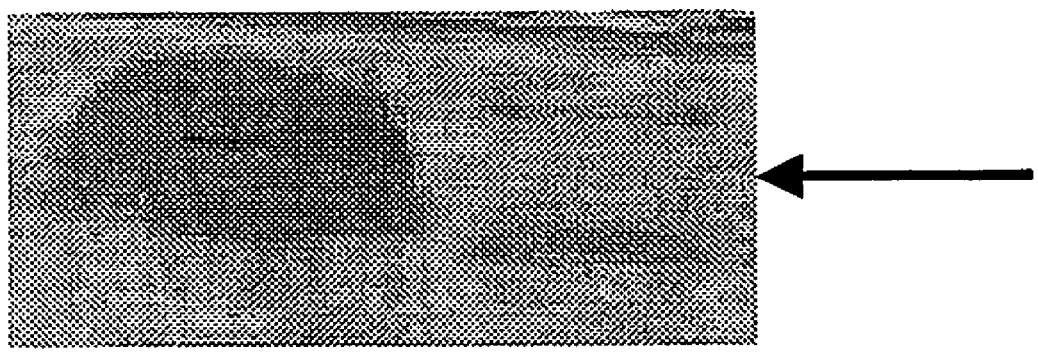
FIG. 2 shows coomasie blue staining of the purified fusion proteins expressed from pSim-2-β-gal vector.
Figure 3A:
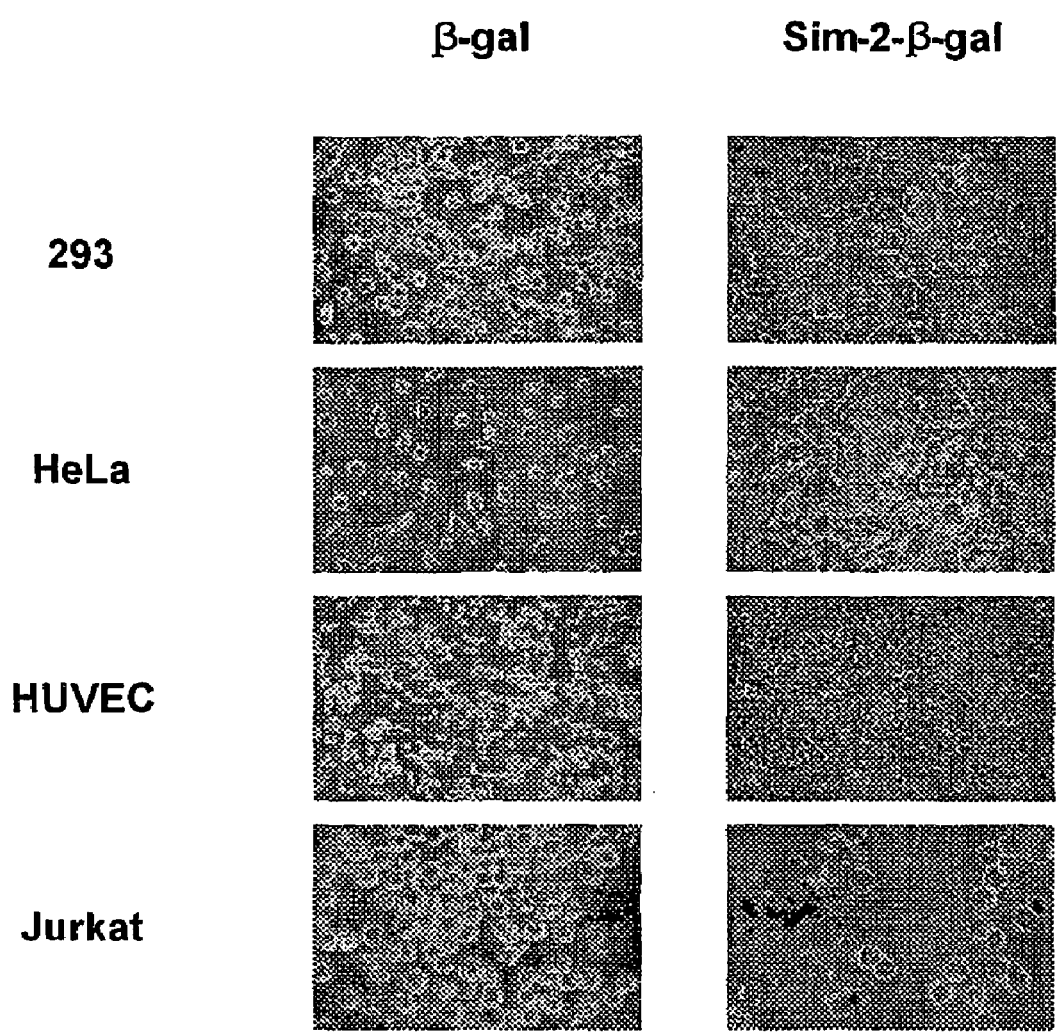
FIG. 3A shows the activity of fusion protein of Sim-2 and β-gal.

HUVEC (ATCC:CRL-1730) (2×10$^5$), HeLa (ATCC: CCL-2) (2×10$^5$), and 293 (ATCC:CRL-1573) (2×10$^5$), which were incubated in 10% FBS (Fetal Bovine Serum) of DMEM, were respectively transferred to Lab-tek II chamber slides. Jurkat cells (ATCC:CRL-10915) (2×10$^5$) incubated in 10% FBS RPMI were transferred to poly-L-lysin coated slide. Each of the slides was treated with the purified 0.5 μM of Sim-2-β-galactosidase for 30 min at 37° C. in 5% CO$_2$ incubator. And the supernatants were removed from the slides. The incubation mixtures were washed using ice-cold PBS four times and then were solidified with 2% formaldehyde solution for 10 min. After removing the solidified solutions, the mixtures were washed again using ice-cold PBS four times. Subsequently, the respective mixtures were treated with 700 μl of β-galactosidase staining solution (Roche. Co.) for 45 min at 37° C. in 5% CO$_2$ incubator. Following the staining, the mixtures were washed with ice-cold PBS four times after removing the supernatants. Next, the mixtures were mounted with 70% glycerol on the microscope slides. The microscopic photographs were displayed in FIG. 3A. As the results, Sim-2 fused β-gal was transduced across the cell membranes of the four kinds of cells very efficiently, while β-gal alone was not transduced at all.

Figure 3B:
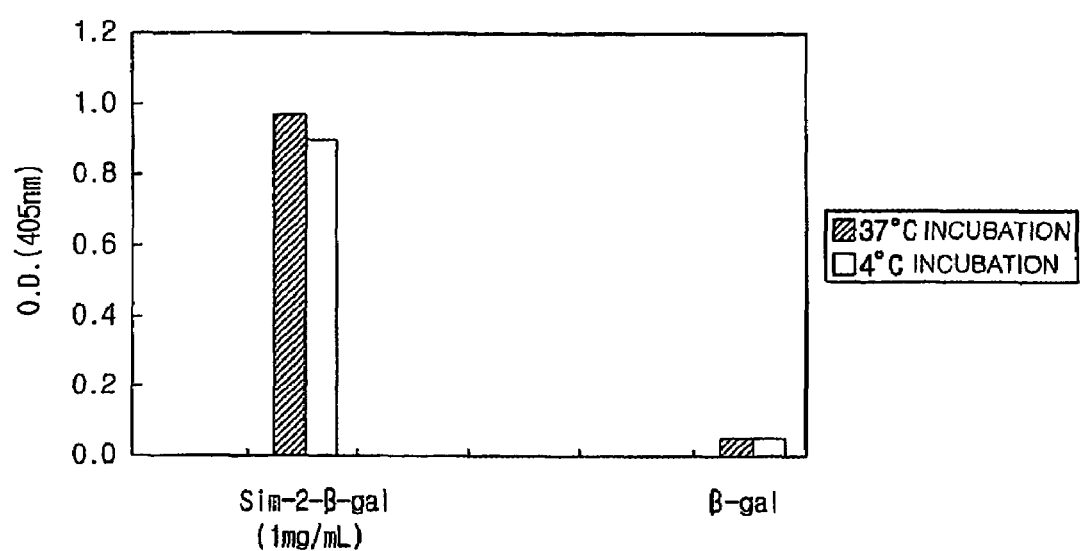
FIG. 3B shows the result of enzyme activity analysis proving that the fusion protein of Sim-2 and β-gal has been effectively transduced into cells.

On the other hand, the transduction of Sim-2-β-gal across cell membrane was detected both at 37° C. and at 4° C., in order to determine whether or not the transduction is carrier-mediated by endocytosis or not. Jurkat cells of 3×10$^6$, which were incubated in 10% FBS (Fetal Bovine Serum) RPMI medium, were washed twice with ice-cold PBS and were suspended in 10% FBS (Fetal Bovine Serum) RPMI medium, and then the soluble fractions of suspension were transferred to 60 mm dishes. The suspension was treated with 1 mg/ml of Sim-2-β-galactosidase for 30 min for both at 4° C. and at 37° C. in 5% CO$_2$ incubator. After washing the suspension including Jurkat cells twice with ice-cold PBS, the suspension was dissolved in 1% NP-40 buffer solution (1% NP-40, 150 mM of NaCl, 10 mM of Tris-HCl, 400 μM of EDTA, 1 mM of Na$_3$VO$_4$, 1 mM of NaF, 10μg of aprotinin, 10 μg of leupeptin). Then, the solution was centrifuged for 20 min at 4° C., and was quantified using the BCA protein assay reagent kit (PIERCE). Thereafter, 20 μg of sample was mixed with 66 μl of β-galactosidase assay buffer [3 μl of 100×Mg$^{2+}$ solution, ONPG (o-nitrophenyl-β-D-galactopiranoside)] and 0.1M of sodium phosphate, and then was subjected to reaction for 30 min at 37° C. followed by the addition of 1 M of Na$_2$CO$_3$ thereto. Absorbance of solution (at 420 nm) was measured three times with microplate reader (Molecular devices) and its mean values and stand deviations were represented in FIG. 3B. As the results, it was observed that Sim-2-β-gal fusion protein was very efficiently transduced across cell membrane both at 37° C. and at 4° C., which clarified that the protein transduction using the Sim-2 of the present invention did not merely result from receptor-mediated endocytosis or phagocytosis.

Example 4

Comparison of Transduction Efficiencies Across Cell Membrane Between Tat and Sim-2

Figure 4A:
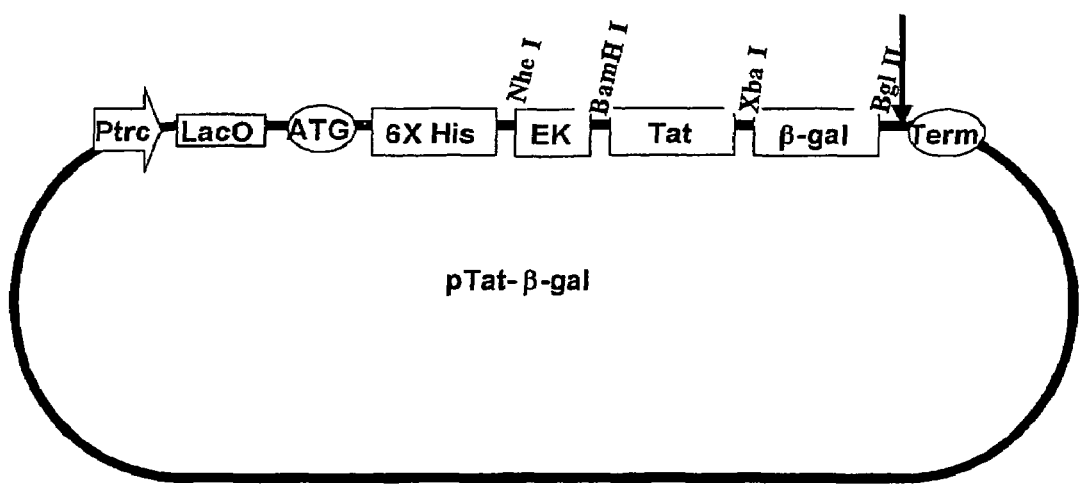
FIG. 4A illustrates the construct of expression vector of pTat-β-gal.
Figure 4B:
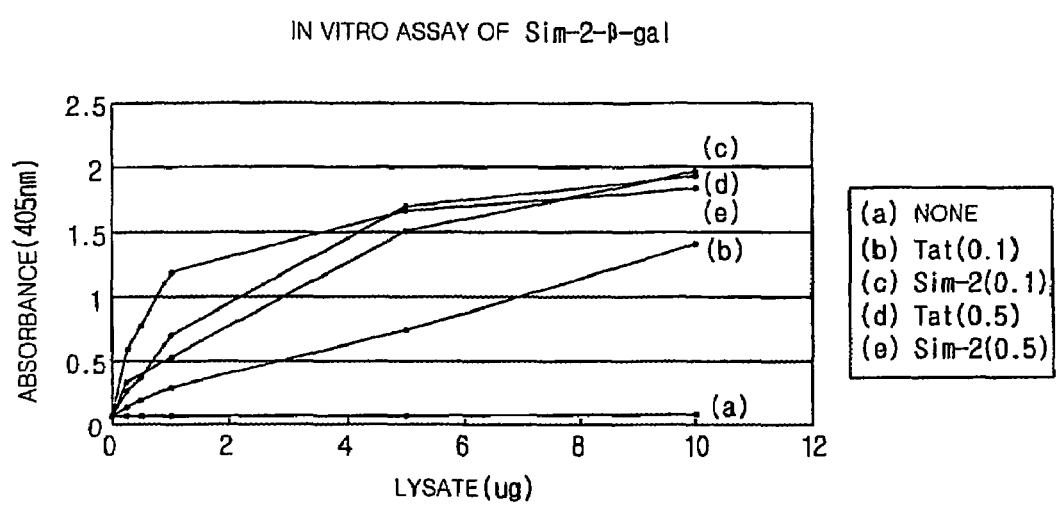
FIG. 4B shows the results of β-gal enzyme activity analysis proving that fusion protein of Sim-2 and β-gal has been more effectively transduced into the cell than the fusion protein of Tat and β-gal.

A pTat-β-gal DNA construct was designed in order to compare the protein transduction efficiencies across cell membrane between the conventional PTD or Tat and Sim-2 of the present invention. For this purpose, nucleic acid sequence encoding β-galactosicase to be used as a reporter and nucleic acid sequence encoding peptide corresponding to amino acids 47 (Tyrosin)–57 (Arginin) from N-terminus of HIV Tat protein were incorporated. Specifically, a primer of SEQ. ID No.:4 containing amino acids from 47$^{th}$ of Tyrosine to 57$^{th}$ of Arginin of N-terminus of Sim-2 and BamHI site was synthesized. And PCR amplification was carried out using pIND/lacZ vector (Invitrogen Inc.), which included total genes of β-galactosidase, as a template, and using a primer of SEQ. ID No.: 3 containing Bgl II site and nucleic acid sequence of 3 -end of β-galactosidase, with pfu turbo DNA polymerase (Stratagene, cat.# 600252-51). The PCR products were cleaved with restriction enzymes of BamHI and BglII, and then purified using Quiaquick PCR purification kit (QIAGEN, cat. #28104). The purified PCR products were cloned to pTrcHis B (Invitrogen, Cat. No V360-20B), which was purified with gel extraction, at BglII site, and was named as pTat-β-gal. FIG. 4A illustrates the constructs. After isolation and purification of Tat-β-gal fusion protein according to the Example 2, transduction efficiencies of Tat-β-gal and Sim-2-β-gal into cells were compared both at 0.1 ug/ml and at 0.5 ug/ml. As disclosed in FIG. 4B, Sim-2 was transduced into the cells more efficiently both at 0.1 ug/ml and at 0.5 ug/ml. Particularly, the transduction efficiency of Sim-2 was significantly superior when 0.1 ug/ml of fusion protein was introduced.

Figure 4C:
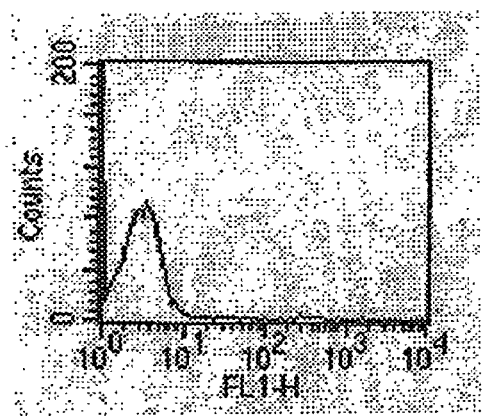
FIG. 4C shows that 7mer of Sim-2-BTM was transduced into Jurkat cells effectively.
Figure 4C:
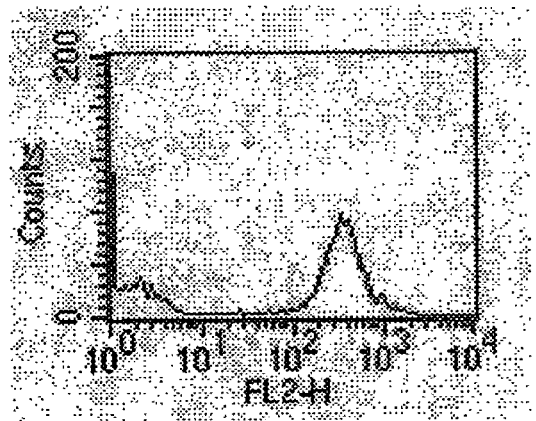

In addition, in order to examine that 7-mer of Sim-2-BTM, in which a part of nucleic acids of Sim-2-BTM was deleted, was transduced into the Jurkat cells efficiently, a peptide was designed by combining 70mer of Sim-2-BTM with a fluorescent material of FITC. After transferring the material into the cells, FACS analysis was carried out. As the results, it was observed that the 7-mer was transduced into the cells effectively (see FIG. 4C).

Example 5

In Vivo Transduction of a Desired Protein Using Sim-2

Figure 5A:
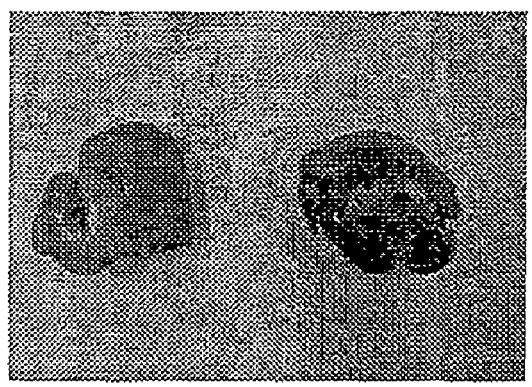
FIG. 5A illustrates the β-gal assay of Sim-2 BTM representing its transducing effects in vivo.
Figure 5A:
Figure 5A:
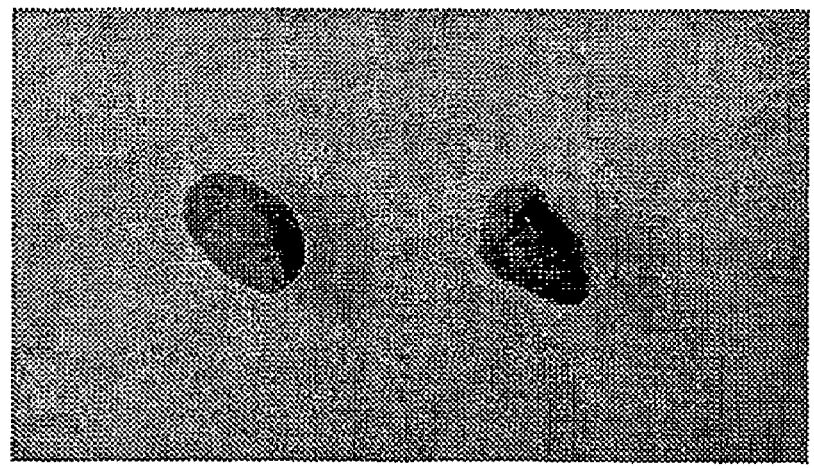

Transduction efficiency of a desired protein using Sim-2 across cell membrane in vivo was detected in this example. In order to detect the efficiency, the isolated and purified 750 ug of Sim-2-β-gal fusion protein of the Example 2 was mixed with PBS, and 500 μl of the mixture was administered by IP (intra peritoneal) injection into 6 months old C57BL/6 mice once a day for 3 days. On the contrary, for the control mice, only the same amount of PBS was administered by IP injection. After 4 hrs from the final injection, the mice were killed and their organs were collected followed by washing with PBS (2 mM of $MgCl_2$). The PBS treated organs were placed on ice-cold 5% formalin. Then, the organs were rinsed with PBS five times, and each of the organs was transferred to β-gal staining solution (Roche. Co.). And, after 12 hrs, the change of color was detected. As disclosed in FIG. 5A, it was observed that β-gal protein was transduced efficiently into kidney, brain, liver, lung and heart, which supported that the target protein was efficiently transferred into organs in vivo using Sim-2-BTM.

Furthermore, it was examined whether the β-gal was transduced by Sim-2 BTM into the cells, which construct the target organs, or was transduced by Sim-2 BTM just to the surface of the organs. In order to carry out this examination, firstly, nucleic acid sequence, which encodes peptide corresponding to amino acids from $558^{th}$ of Alanine to $566^{th}$ amino acid of Arginin from N-terminus of human transcription factor of Sim-2 (genebank code: U80456), and nucleic acid sequence encoding a reporter of eGFP (enhanced Green Fluorescent Protein) were combined. For the combination, a primer of SEQ. ID No.: 2 containing amino acids from $558^{th}$ of Alanine to $868^{th}$ amino acid of Arginin from N-terminus of human transcription factor of Sim-2 and BamHI site, and a primer of SEQ. ID No.:5 containing Bgl II site for cloning and nucleic acid sequence of 3'-terminus of eGFP were synthesized. Then, PCR amplification was carried out using pEGFP-N1 vector (Invitrogen Inc.) comprising total eGFP genes, as a template, with pfu turbo DNA polymerase (Stratagene, cat.# 600252-51).

The PCR products were treated with restriction enzymes of BamH I and BglII, and were purified using the Quiaquick PCR purification kit (QIAGEN, cat.# 28104). Next, the purified PCR products were cloned to pTrcHis B (Invitrogen Inc., Cat. No V360-20B), which was extracted with the gel extraction, at Bgl II site. The obtained recombinant expression vector was named as p Sim-2-eGFP. According to the Example 2, Sim-2-eGFP, which was expressed in DH5a, was isolated and purified, and then was administered by intraperitoneal injection to the mice. After 4 hrs from the injection, the spleen was removed surgically and was crushed. Splenocytes were isolated from the crushed spleen. Then, FACS analysis was carried out to monitor the eGFP that was transduced into the cells (see FIG. 5B). As disclosed in FIG. 5B, it was observed that the eGFP, which was transduced to spleen by Sim-2 BTM, was also transduced efficiently to the splenocytes that constructs the spleen.

Furthermore, it was examined that the desired protein was transduced by Sim-2 BTM to organs in vivo via blood. 500 μl of the mixture of the isolated and purified 750 μg of Sim-2-β-gal fusion protein and PBS was administered to 6 months old C57BL/6 mouse once a day for three days by I.P. (intraperitoneal), IV (intravenous), SC (subcutaneous) or nasal route. Whereas, the control mice were given the same amount of PBS alone by I.P. After collecting blood from mouse injected with the fusion proteins, T cells were isolated using MACS and anti-CD3 mAb, and then the activity of β-galactosodase was detected as disclosed in the Example 3. The results are displayed in FIG. 5. As the results, the fusion proteins were administered efficiently by the Sim-2 BTM through numerous administration routes, such as IP, IV, SC and nasal routes, to the T cells in blood.

Figure 5B:
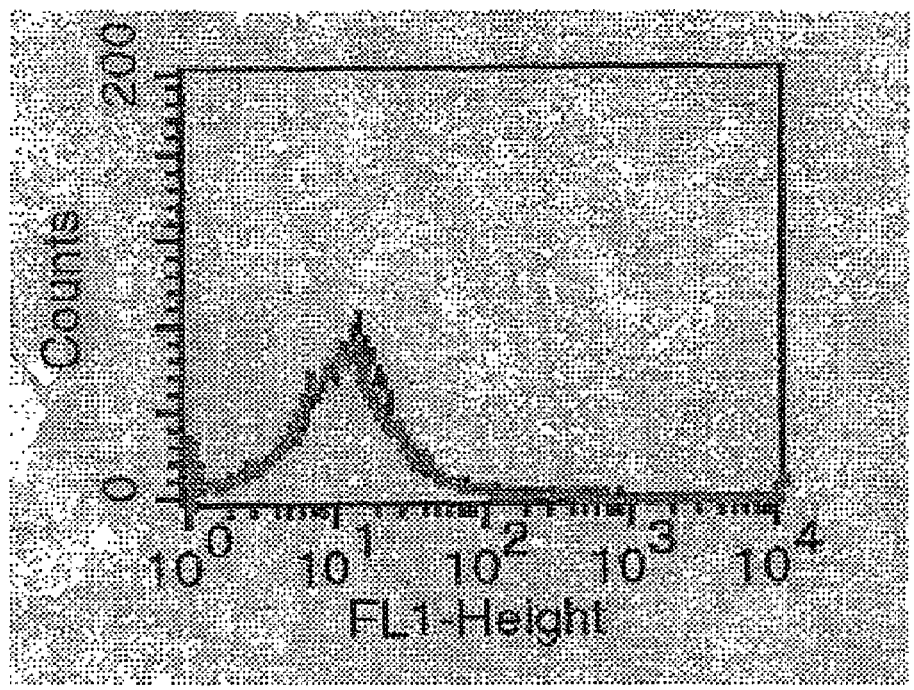
FIG. 5B represents transduction efficiency of eGFP into spleen cell using Sim-2 BTM.
Figure 5B:
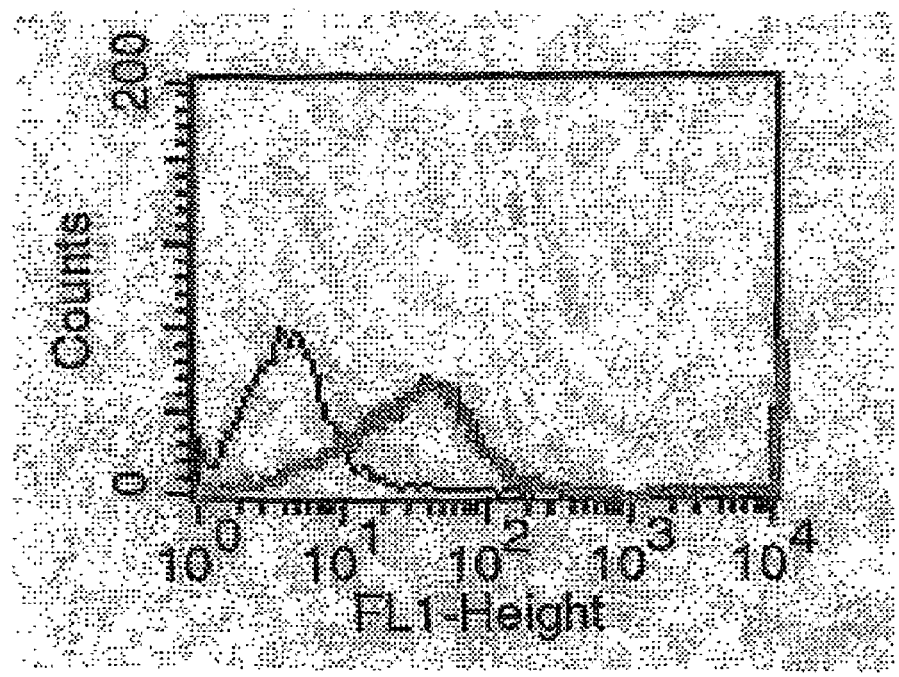
Figure 5C:
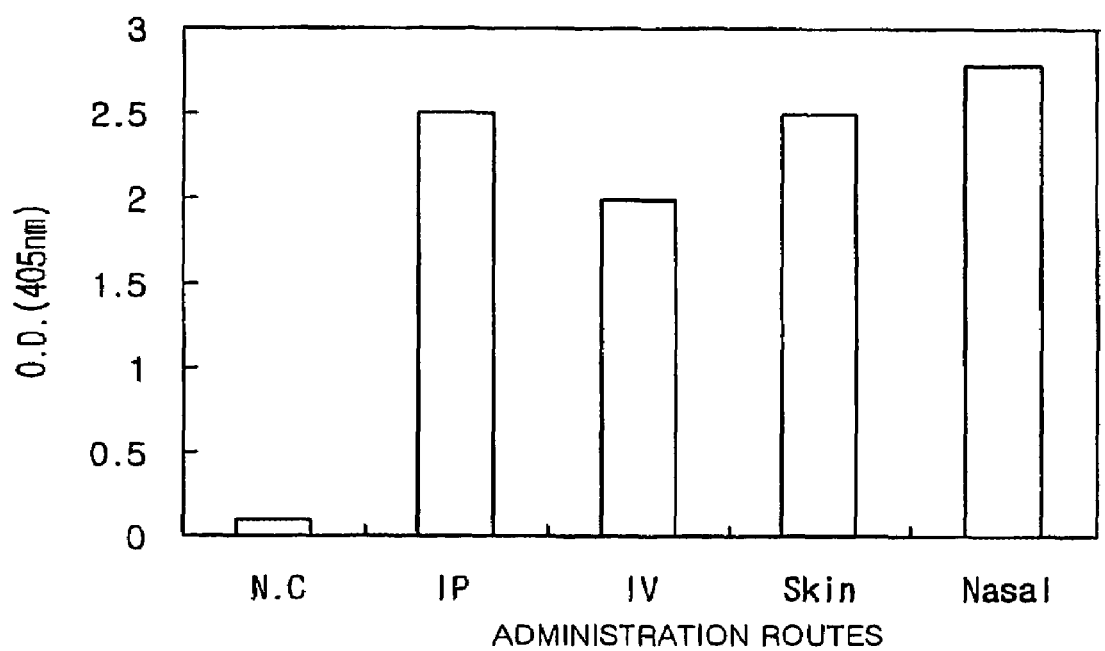
FIG. 5C represents the transduction of β-gal into T cells in blood via numerous administration routes.
Figure 5D:
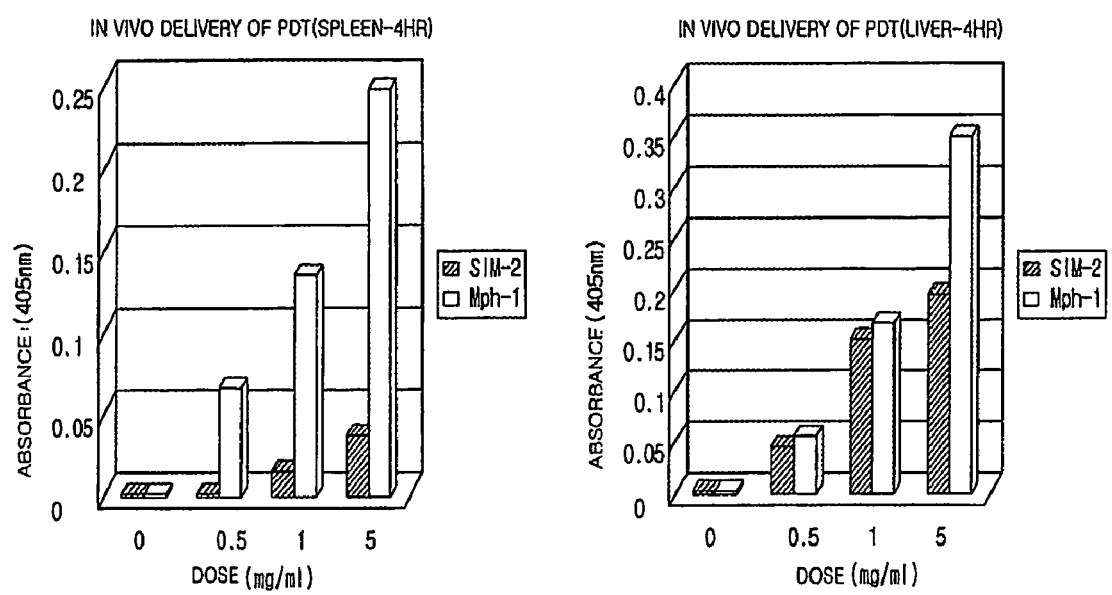
FIG. 5D represents the efficiency of transduction of β-gal into liver cells.

Furthermore, transduction efficiencies of the desired macromolecules among the organs in vivo were investigated and analyzed. Different concentrations of the isolated and purified Sim-2-β-gal fusion protein were administered to 6-month old C57B/6 mice by IP injection, as disclosed in the Example 2. After 4 hrs from the injection, the transduction efficiencies between liver and spleen were compared. FIG. 5B shows efficient transfer into the spleen. As the results, the Sim-2-BTM was introduced into the spleen more efficiently in comparison to liver at the concentration of 1 nM. Thus, it was verified that Sim-2-BTM selectively transferred the macromolecules into the liver.

Example 6

Figure 6A:
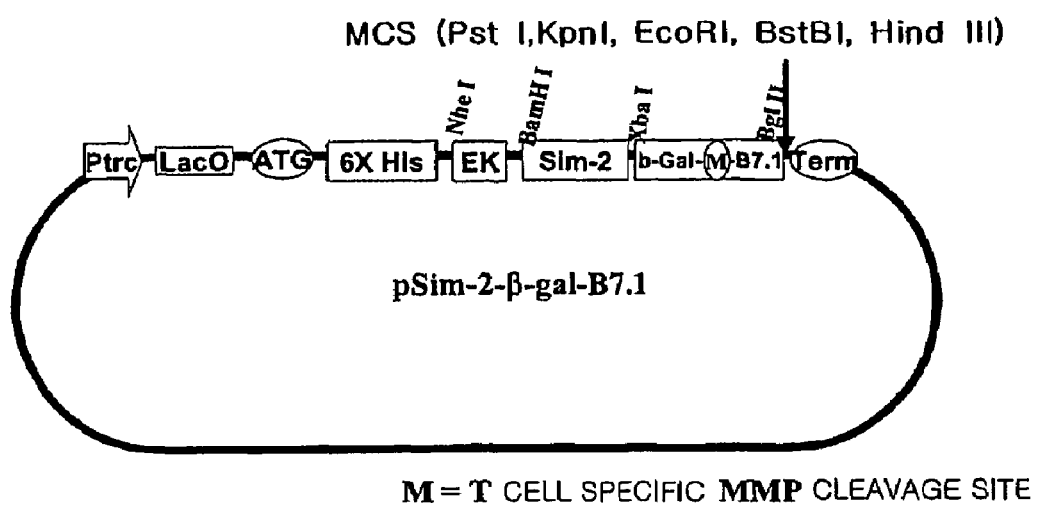
FIG. 6A illustrates the recombinant expression vector of pSim-2-β-gal-B7.1.
Figure 6B:
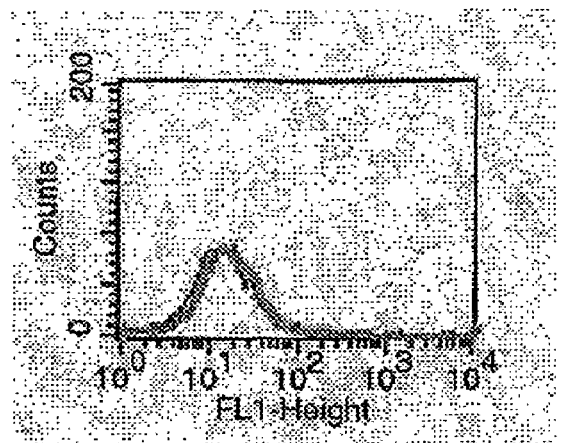
FIG. 6B shows the results of FACS analysis, representing that the desired molecule of β-gal is specifically transduced into T cells.
Figure 6B:
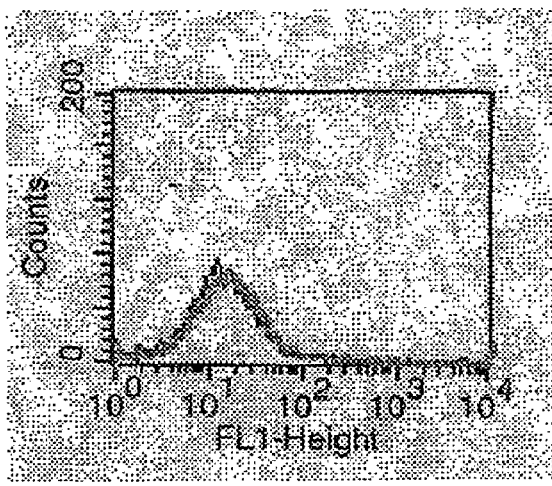
Figure 6B:
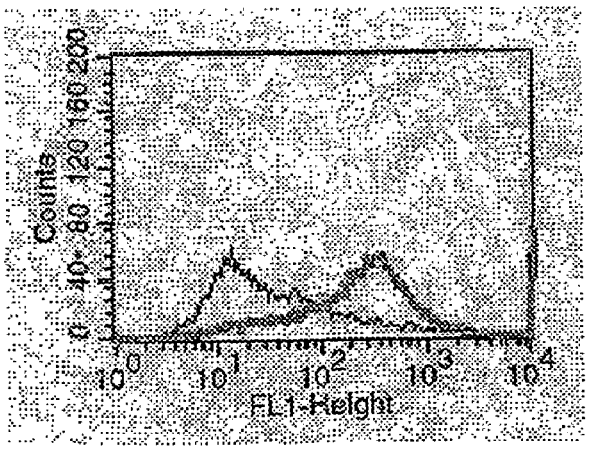

Cell Specific Transduction of Fusion Protein Between Sim-2 and a Desired Protein In order for the desired protein of Sim-2-β-gal according to the Example 2 to be introduce to a specific cell selectively, a ligand or a receptor that exists specifically in cell, tissue or organ to which the protein is transduced, was employed in this example. For example, in order to transduce the desired protein to T cell, an expression vector of pSim-2-β-gal-B7.1 was designed by inserting amino acid sequence of MMP (MatrixMetalloprotease) cleavage site, which was present on extracellular matrix and was attached to cell membrane, into Sim-2-β-gal at 3' region, and then by cloning B7.1 of ligand of T cell specific CD28 receptor, next to the 3' region. In addition, expression vector of pSim-2-β-gal-B7.1 was generated by carrying out PCR amplification using cDNA mixture of human primary T cells that were manufactured in our laboratory, as a template, and using a primer of SEQ. ID No.:6 containing BamH I site and N-terminus of B7.1, and a primer of SEQ. ID No.:7 containing Bgl II site and C-terminus of B7.1, and carrying out molecular cloning according to the Example 1. FIG. 6A represents the construct of the expression vector of pSim-2-β-gal-B7.1. After transforming DH5a with the pSim-2-β-gal-B7.1 expression vector in the Example 2, fusion protein of Sim-2-β-gal-B7.1 was isolated and purified from the cell culture. After 4 hrs from the I.P. injection of the fusion protein to a mouse, T cells were collected from blood to detect activity of β-gal. As disclosed in FIG. 6B, relatively high β-gal activity was observed in T cells, while little β-gal activity was observed in B cells. This results supported that Sim-2-β-gal fusion protein was transduced to T cell specifically, after the binding between B7.1 of the fusion protein and T cell CD28 or CTLA-4 followed by cleavaging of the fusion protein by MMP existing on the surface of T cell.

Example 7

Intracellular Transduction of DNA (CD8-ζ) Using Sim-2 BTM (STEP 1) Preparation of Expression Vector Including Fusion Genes of Sim-2 and Gal4

Figure 7:
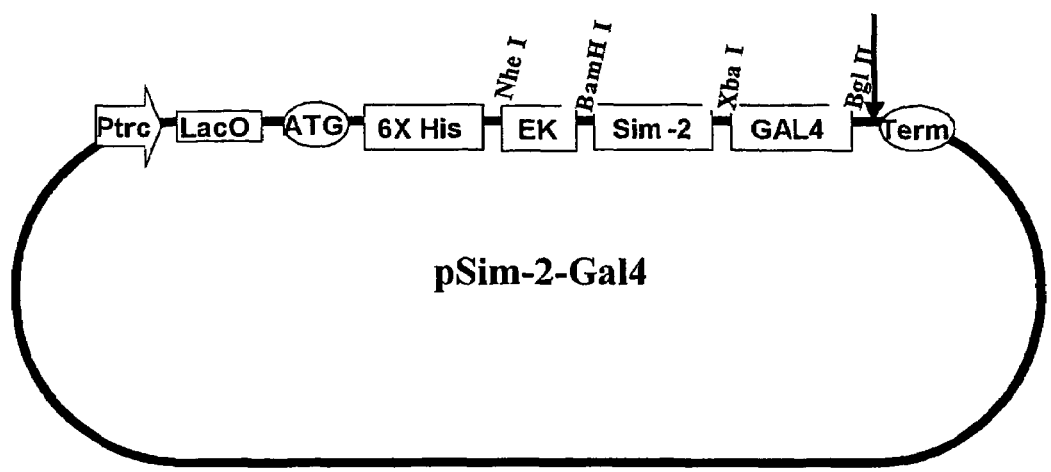
FIG. 7 illustrates the construct of recombinant expression vector of pSim-2-Gal4.

The pSim-2-β-gal vector of the Example 1 was treated with restriction enzymes, XbaI and BglII, to remove β-galactosidase gene therefrom. Then, pSim-2-Gal4 plasmid was developed by carrying out conventional PCR amplification and molecular cloning, as disclosed in the Example 1, using a primer of SEQ. ID No.:8 having N-terminal sequence of GAL4 DNA binding protein and XbaI restriction enzyme site, and a primer of SEQ. ID No.:9 having N-terminal sequence of GAL4 DNA binding protein and Bgl II restriction enzyme site. FIG. 7 illustrates the construct of the expression vector of pSim-2-Gal4.

Figure 8:
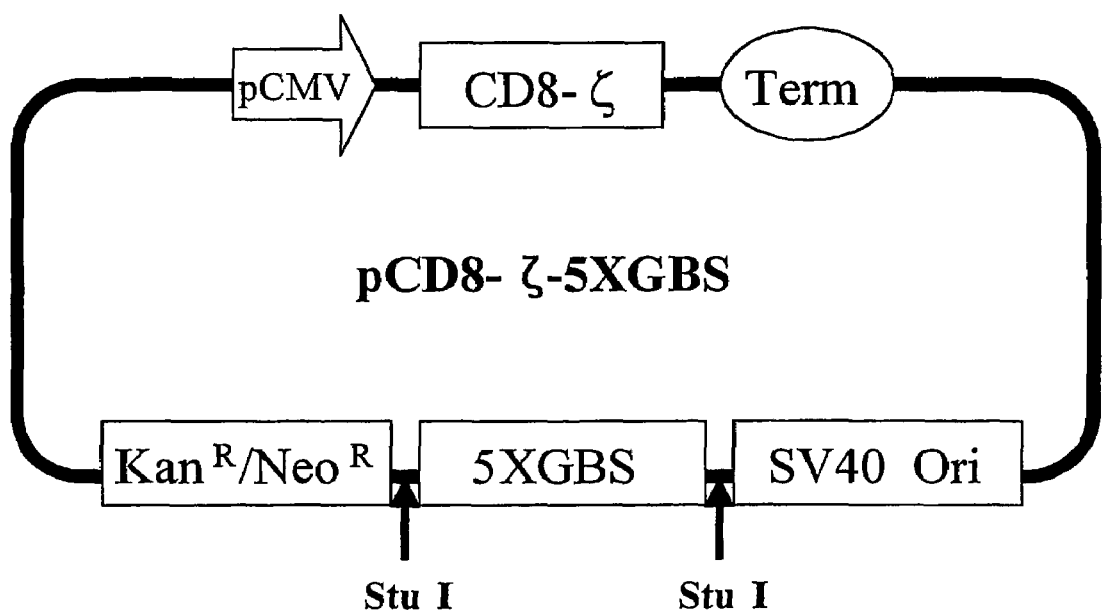
FIG. 8 illustrates the construct of recombinant expression vector of pCD8-ζ-5×GBS (Gal4 binding sequence).

(STEP 2) Preparation of Expression Vector of pCD8-z-5×GBS Having DNA Sequence to Which Gal4 DNA Binding Protein Binds Specifically In order for the binding of Sim-2-Gal4 of the Example 1 to be carried out more efficiently, pCD8-z-5×GBS was designed by cloning 5 (five) successive GBS sequence at the StuI restriction enzyme recognition site of pcDNA3-CD8-z, which was prepared by inserting CD8-ζ to pcDNA3 expression vector (Invtrogen Inc.) at restriction enzyme recognition sites for XbaI and BamHI. Specifically, nucleic acid sequence corresponding to GBS was synthesized using a primer and hybridized, and then was cloned to pCD8-ζ at StuI recognition site of 3' terminus. FIG. 8 illustrates the structure of expression vector of pCD8-ζ-5×GBS. The nucleic acid sequence of GBS was designated as SEQ ID No.10.

(STEP 3) Confirmation of the Transduction of CD8-ζ DNA Using Sim-2

Figure 9A:
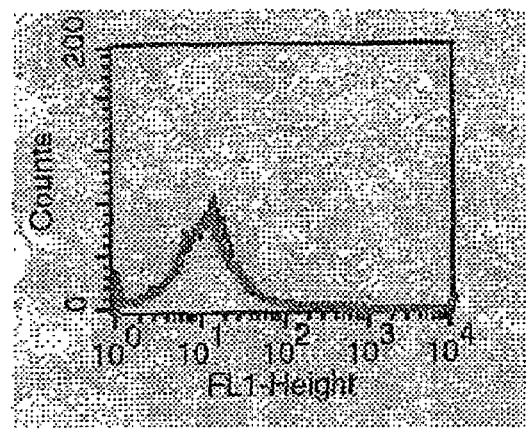
FIG. 9A represents the transduction of expression vector of pCD8-ζ-5×GBS into T cells usinf Sim-2 BTM.
Figure 9A:
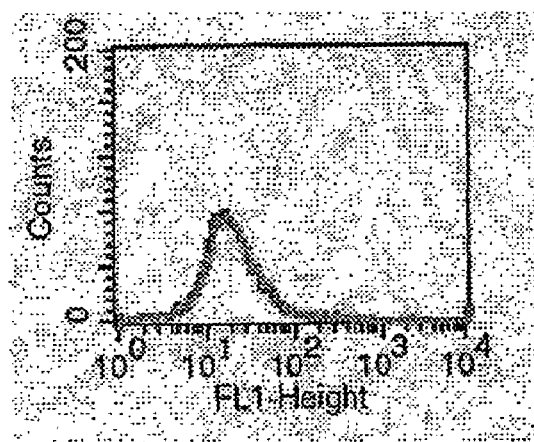
Figure 9A:
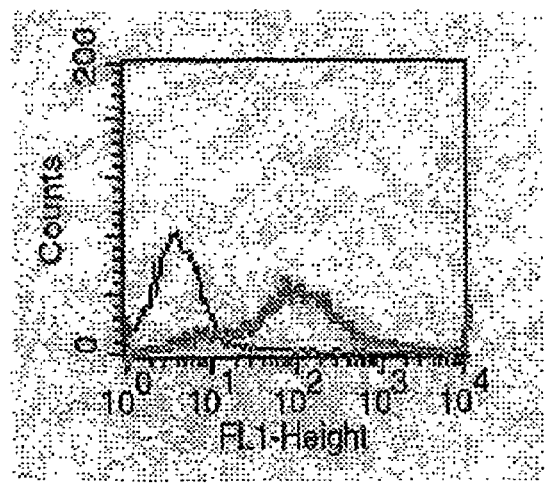

Gal4s of Sim-2-Gal4 fusion proteins were respectively binded to each of the five GBSs of pCD8-ζ-5×GBS. The expressed and purified Sim-2-Gal4 fusion protein in the Example 2 was bound to pCD8-ζ-5×GBS DNA prepared in the step 2 using the expression vector of pSim-2-Gal4 manufactured in the step 1 at room temperature. After mixing the fusion complex with PBS, the mixture was introduced to $10^7$ of primary T cells, and then was incubated for 48 hrs at 37° C. in order to induce over-expression of CD8-ζ fusion proteins elicited by DNA constructs delivered into the cells. In order to determine the over-expression of CD8-ζ fusion protein on the cell surface, FACS (Fluorescence-Activated Cell Sorter) analysis was carried out using OKT8 (ATCC No. CRL-8014) of a monoclonal antibody to CD8 (Current Protocol for Immunology). FIG. 9A discloses the results. As shown in FIG. 9A, CD8-ζ fused with Sim-2 biomolecule transduction peptide was trasduced into the cells across the cell membrane. As negative controls, the expressions of CD8-ζ chimeric molecules in T cells, which include Sim-2-Gal4 fusion proteins not having pCD8-ζ-5× GBS or including pCD8-ζ-5×GBS alone, were analyzed using FACS. As the results, the desired DNA construct to be transduced into the cell was bound to binding sequences of DNA binding protein, thereby the DNA binding protein fused to Sim-2 efficiently transferred the desired DNA construct across the cell membrane for the expression of the DNA construct.

Figure 9B:
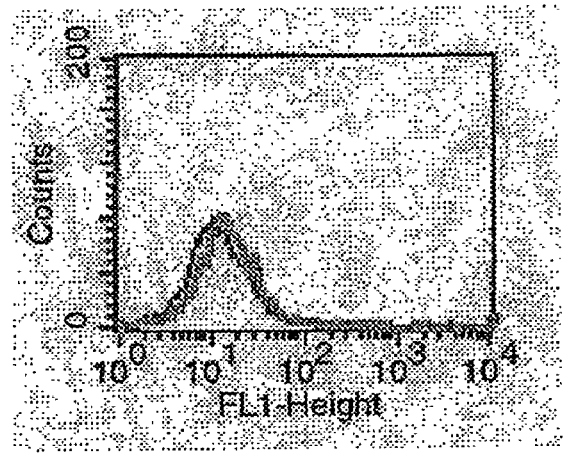
FIG. 9B represents the transduction of expression vector of pCD8-ζ-5×GBS into T cells and splenocyte in blood in vivo and the expression thereof.
Figure 9B:
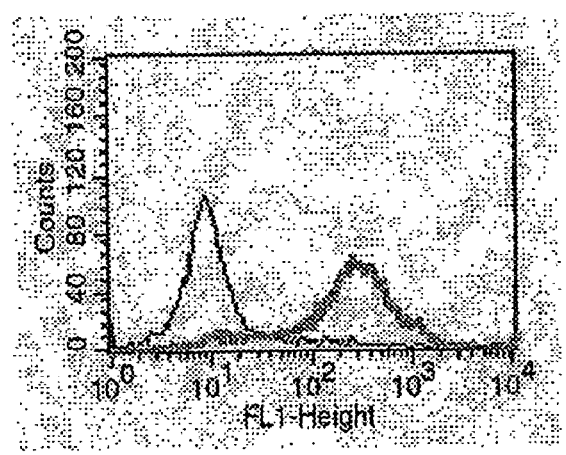
Figure 9B:
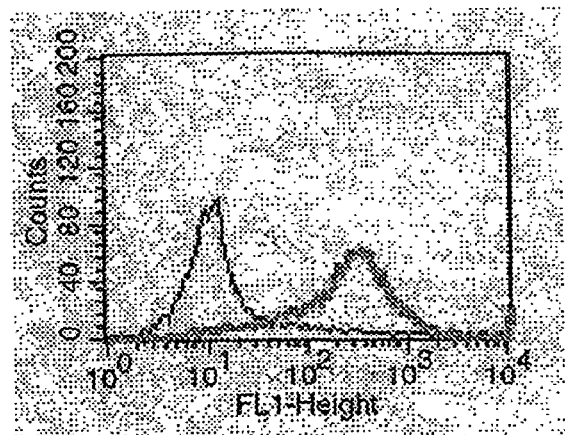

In addition, in this example, the transduction of DNA using Sim-2 BTM was examined in vivo. For this purpose, a complex between Sim-2-Gal4 fusion protein, which was fused at room temperature, and pCD8-ζ-5×GBS was administered by I.P. injection into a mouse, and then, after 48 hrs from the injection, T cells in blood were collected using T cell specific anti-CD2 mAb and MACS, as disclosed in the Example 5. Thereafter, splenocytes of spleen were isolated and the level of expression of CD8-ζ chimeric proteins on the surface of the splenocytes was detected with FACS. The results are displayed in FIG. 9B. As the results, the expression vector of pCD8-ζ-5×GBS, which was transduced in vivo into the cell using Sim-2 BTM and Gal4, was effectively transduced not only into T cells but also into splenocytes of the spleen.

Example 8

T Cell Specific Transduction and Expression of pCD8-ζ DNA (STEP 1) Preparation of an Expression Vector Including Genes of Sim-2, Gal4 and B7.1

Figure 10A:
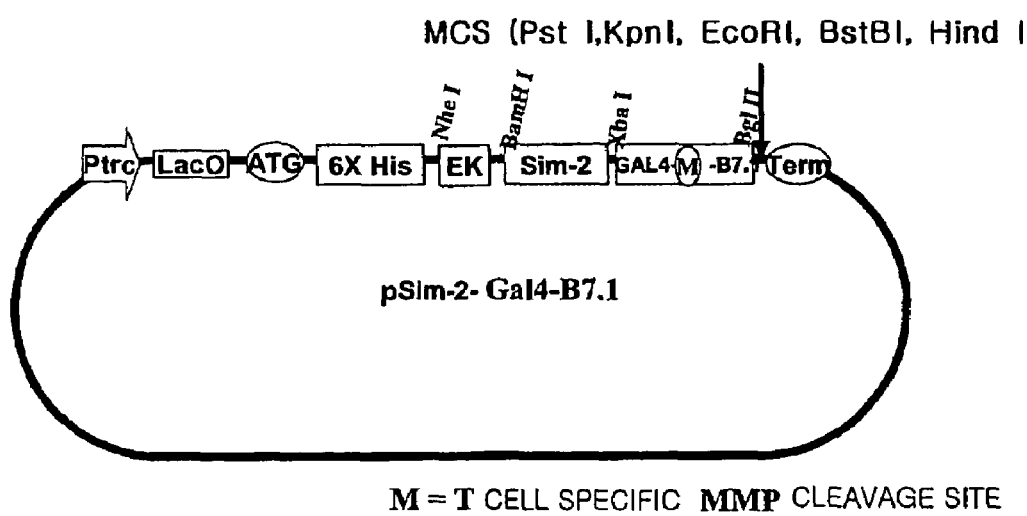
FIG. 10A illustrates the construct of expression vector of pSim-2-Gal4-B7.1.

T cell specific transduction of pCD8-ζ DNA using Sim-2 was examined in this example. T cell specific MMP cleavage site was cloned to pSim-2-Gal4 of the Example 7 at 3' region, according to the Example 6, and then ecto domain of B7.1 was inserted thereto with conventional PCR amplification and molecular cloning using T cell cDNA mixture, which was prepared in our laboratory, as a template, and using primers (SEQ. ID No.: 6 and 7), as disclosed in the Example 1. Thereby, pSim-2-Gal4-B7.1 DNA construct was generated (see FIG. 10A).

Figure 10B:
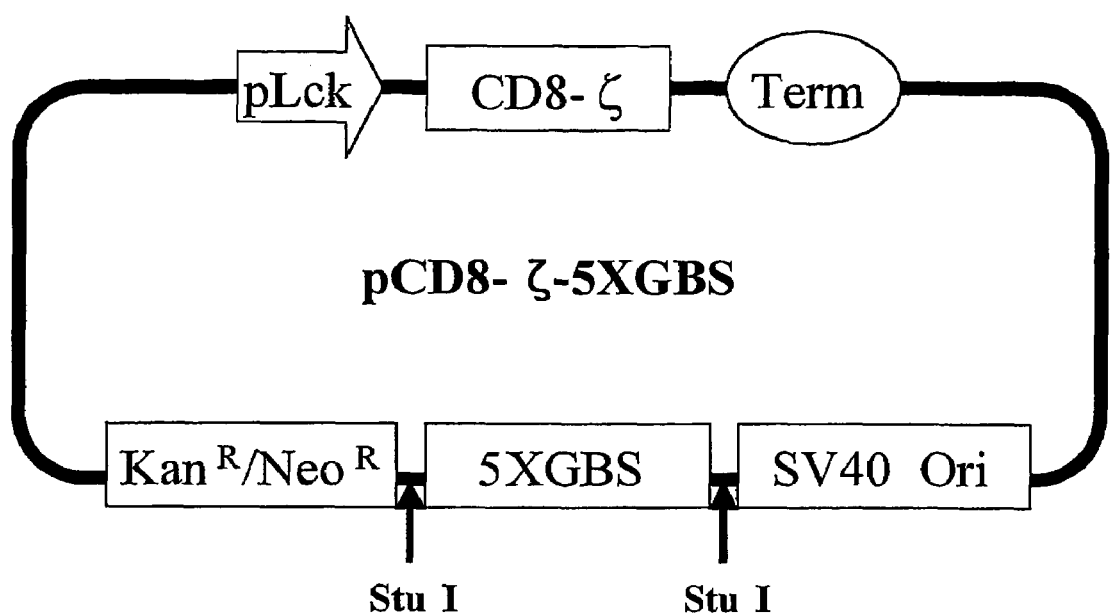
FIG. 10B illustrates the construct of expression vector of pLCD8-ζ-5×GBS.

(STEP 2) Preparation of Expression Vector Comprising T Cell Specific Promoter of Lck, pLCD8-ζ and 5 (Five) GBSs The CMV promoter, which was designed in step 2 of the Example 7, was replaced by a T cell specific lck promoter at HindIII recognition site using conventional molecular cloning method. FIG. 10B illustrates the construct of expression vector of pLCD8-ζ-5×GBS.

(STEP 3) T Cell Specific Transduction of pCD8-ζ-5×GBS DNA Using Sim-2

Figure 10C:
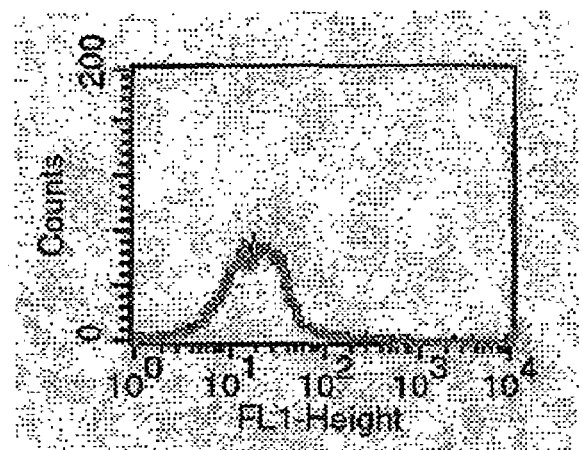
FIG. 10C represents T cell specific transduction of expression vector pCD8-ζ-5×GBS using Sim-2 BTM.
Figure 10C:
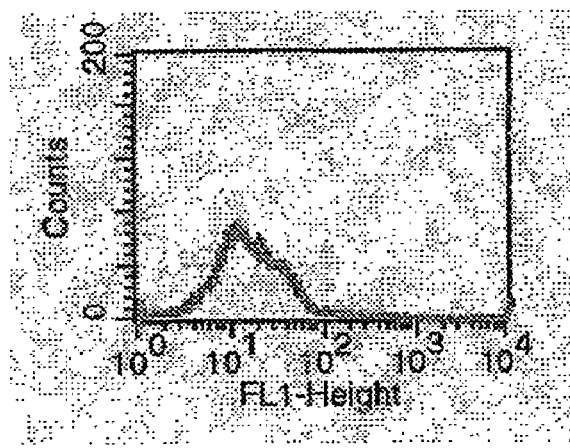
Figure 10C:
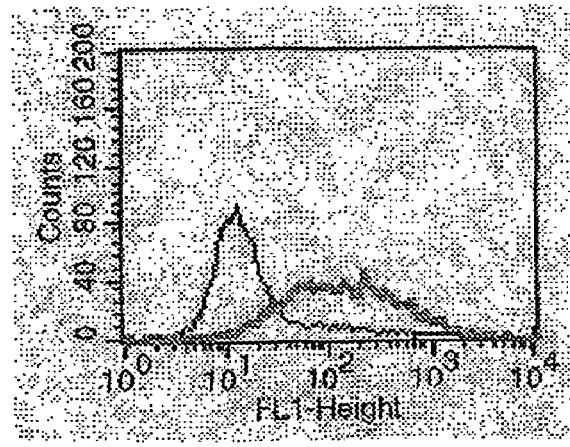

The pCD8-ζ-5×GBS, which was designed in step 2 of the Example 7, was specifically transferred in vivo into a T cell in this Example. A complex of Sim-2-Gal4-B7.1 fusion protein, which was purified and expressed as disclosed in the Example 7, and the expression vector of pCD8-ζ-5×GBS was prepared at room temperature. After 48 hrs from IP injection of the mixture of complex and PBS to a mouse, T cells and B cells in blood were collected using anti-CD2 mAb and anti-B220 mAb, respectively, with MACS from the mouse. Then, the expression level of surface chimeric molecule of CD8-ζ was examined with FACS using anti-CD8 mAb of OKT8 (see FIG. 10C). As the results, the expression vector of pCD8-ζ-5×GBS was firstly relocated around T cells by the binding between extra-cellular portion of Sim-2-Gal4-B7.1 fusion protein and CD28 or CTLA-4, which were present on the surface of T cell, and then was cleaved by MMP on the surface of T cells. Thereby, the complex of Sim-2-Gal4 and pCD8-ζ-5×GBS was efficiently transduced into T cells and expressed therein, while the CD8-z chimeric molecules were not expressed in B cells, since there were no expression vector transferred into B cells.

(STEP 4) T Cell Specific Expression of pLCD8-ζ-5×GBS DNA Using Sim-2

In order for the expression vector in step 2 in this Example to be expressed in T cell specific ways using Sim-2-Gal4 fusion protein in step 2 in the Example 7, firstly, a complex of Sim-2-Gal4 and pLCD8-ζ-5×GBS, which was manufactured at room temperature as disclosed in above step 3, was transferred in vivo into cells. After 48 hrs from IP injection of the mixture of complex and PBS to a mouse, T cells and B cells in blood were collected using anti-CD2 mAb and anti-B220 mAb, respectively, with MACS from the mouse.

Figure 10D:
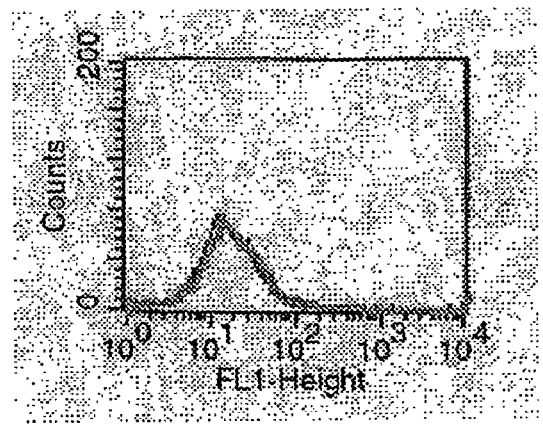
FIG. 10D represents T cell specific expression of expression vector pLCD8-ζ-5×GBS using Sim-2-BTM.
Figure 10D:
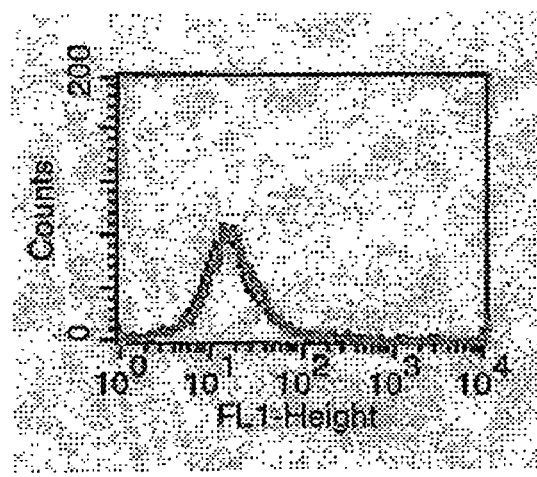
Figure 10D:
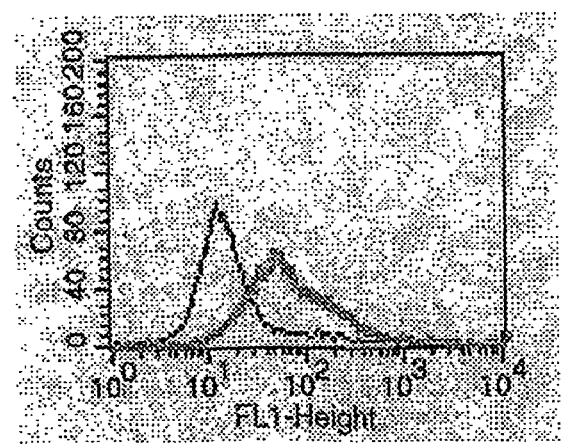

Then, the expression level of surface chimeric molecule of CD8-ζ was examined with FACS using anti-CD8 mAb of OKT8 (see FIG. 10D). As the results, the T cell specific expression of the expression vector of pLCD8-ζ-5×GBS was observed.

Example 9

Figure 11A:
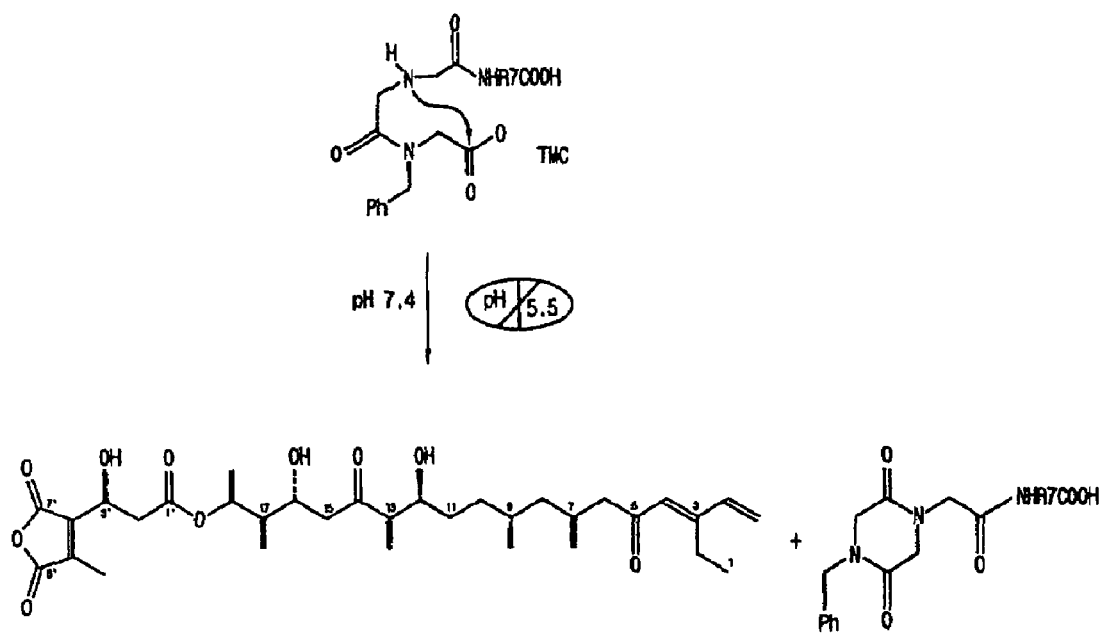
FIG. 11A shows the structure of pH sensitive chemical linker between Sim-2-BTM and TMC, an immuno-suppressor.
Figure 11B:
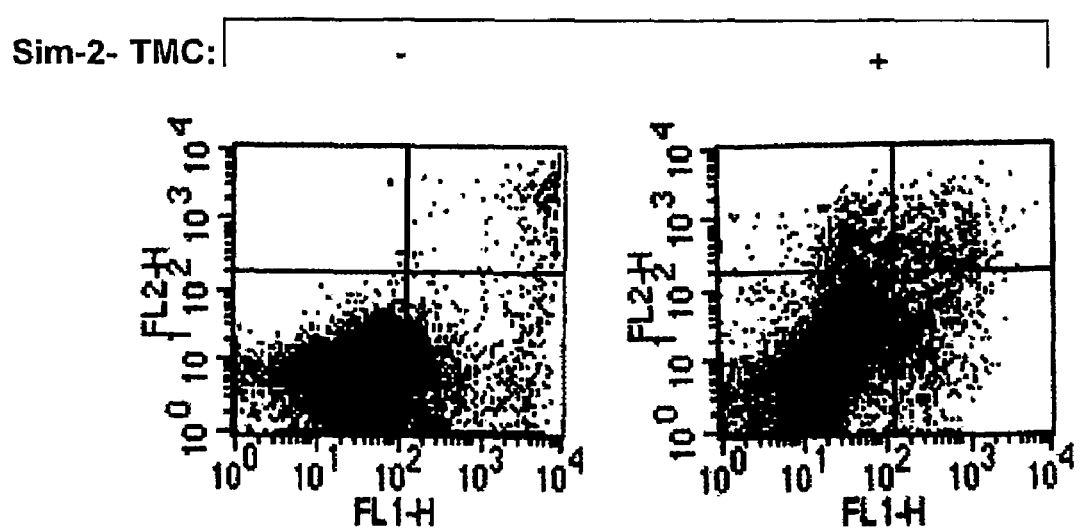
FIG. 11B shows the transduction of TMC into Jurkat T cells by Sim-2-BTM.

Intracellular Transduction of Fusion Complex Between Sim-2 and T Cell Specific Immunosuppressor of TMC A fusion protein of Sim-2 and extra-cellular portion of B7.1 was designed in order to transduce various kinds of chemical compounds having biological activities in vitro and in vivo. An expression vector of pSim-2-B7.1 was designed using mouse T cell cDNA library, which was manufactured in our laboratory, as a template, and using a primer of SEQ. ID No.:11 comprising BamHI restriction enzyme site, Sim-2 BTM and N-terminal nucleic acid sequence of B7, and a primer of SEQ. ID No.:12 comprising Bgl II restriction enzyme site and C-terminal nucleic acid sequence of B7. T cell specific MMP cleave site was introduced to between Sim-2 and B7.1. Sim-2-B7.1 fusion protein, which was expressed and purified from DH5a, was bound to TMC (tautomycetin) using pH sensitive chemical linker as illustrated in FIG. 11. Jurkat T cells were treated with 0.1 ug/ml of the TMC-Sim-2-B7.1 complex. After 5 hrs from the treatment, TMC induced Jurkat T cell apoptosis was analyzed with FACS using PI staining [I. Schmid et. al Cytometry 13:204-208 (1992)] (see FIG. 11B). As the results, it was observed that the TMC compounds, which were transferred into the Jurkat T cells using Sim-2-B7 fusion proteins, elicited apoptosis effectively.

Furthermore, immunosuppressive effects of TMC-Sim-2-2-B7.1 in vivo were examined and analyzed. The immunosuppressive effect in vivo of TMC-Sim-2-2-B7.1 was determined using organ rejection animal model of rat heterocardiac allograft rejection (Jae-Hyuck Sim et al. PNAS vol. 99, no. 16, 10617-10622, 2002). Table 1 shows the results.

TABLE 1

| Drugs | Concentration (mg/kg) | Administration | Days kept alive | Number of rats |
|---|---|---|---|---|
| Cremophor | 5 | I.P. | 9 | 4 |
|  | 5 | I.P. | 10 | 3 |
| CsA/ Cremophor | 5 | I.P. | >100 | 2 |
| Sim-2-TMC/PBS | 0.07 | I.P. | >160 | 10 |
| Sim-2-TMC/PBS | 0.09 | Skin | >160 | 11 |

As the results, the transplanted organs of the organ rejection animal models, which were given TMC-Sim-2-B7.1 complex by IP injection (0.07 ug/ml) or by subcutaneous administration (0.09 ug/ml), operated 160 days or more, while the transplanted organs of the organ rejection animal models, which were given conventional immunosuppressor of CsA (cyclosphorin A) by IP injection, operated 100 days or more. On the other hand, the transplanted organs of the organ rejection animal models, which were given cremophor by IP injection, operated only 9 or 10 days.

Example 10

Immunosuppressive Effects In Vivo of Sim-2-zA1A2 and Sim-2-CTLA-4 Protein Drugs

Figure 12:
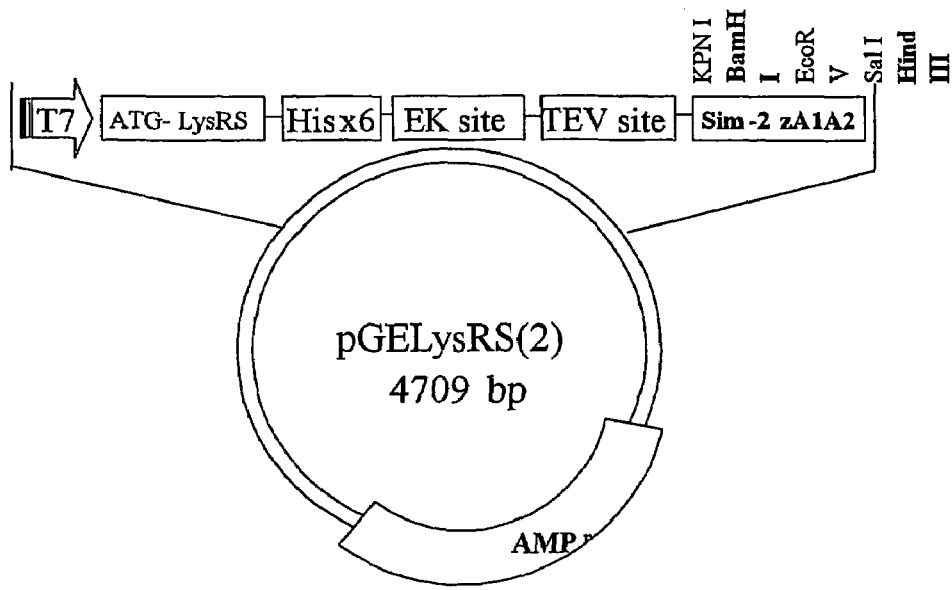
FIG. 12 illustrates the construct of expression vector of pSim-2-zA1A2(a) and pSim-2-CTLA4(b).
Figure 12:
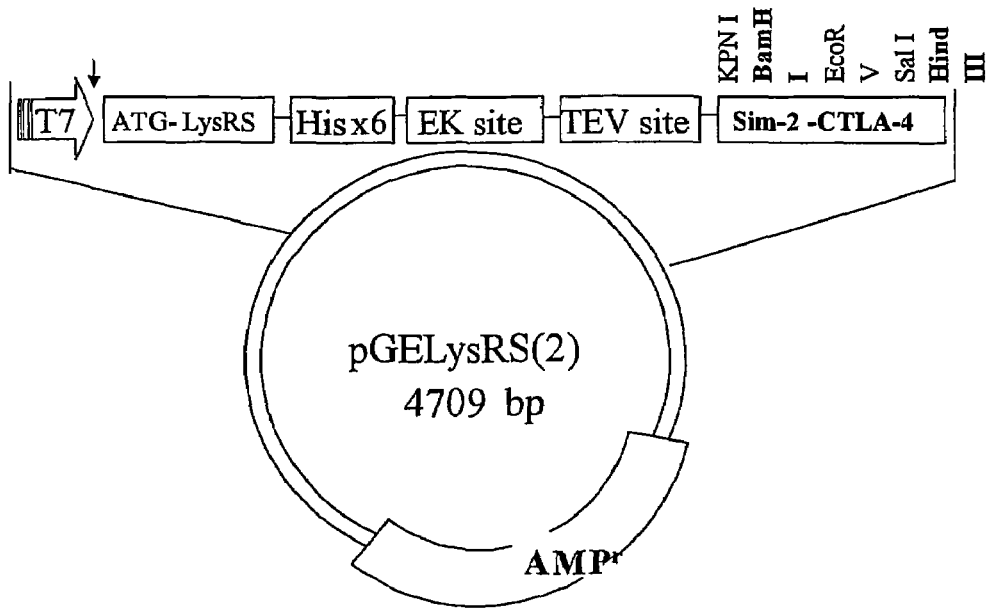

As confirmed in the example disclosed above, it was proved that Sim-2 BTM can efficiently transfer numerous materials, which control in vivo various physiological responses, such as proteins, DNA and/or RNA and chemical compounds, into numerous organs or cells constructing the organs by binding the materials covalently or non-covalently. Thus, in this example, a new type of protein drug, which could regulate immune response in vivo, was provided by introducing wild type or mutant protein that regulated intracellular signal transduction, using the Sim-2 BTM. As a desired protein inhibiting immune response elicited by T cell, cytoplasmic domain of z chain of a signal transduction chain of TcR complex, which recognizes in vivo both a portion of antigenic peptide and MHC, thereby transfers activation signal into the cells, was selected in this example. We, inventors, verified in the preliminary study the fact that when over-expressing zA1A2 type, which was prepared by substituting Tyrosin with Phenylalanin at $1^{st}$ ITAM of cytoplasmic domain of TCR z chain, the T cell activation signals were significantly blocked (Wook-Jin Chae et al. JBC 2003). Based on such results, an expression vector was prepared by fusing Sim-2 BTM and zA1A2 type of TcR z chain. FIG. 12(a) illustrates the construct. In order to make this expression vector, a 5' primer of SEQ. ID No.:13 comprising nucleic acid sequence of Xba I restriction enzyme, nucleic acid sequence of Sim-2 BTM and N-terminal nucleic acid sequence of cytoplasmic domain, and a 3' primer of SEQ. ID No.:13 comprising nucleic acid sequence of Hind III site and C-terminal nucleic acid sequence of z chain were prepared. Then, PCR amplification was carried out using pcDNA3-zA1A2 expression vector synthesized in our laboratory (Wook-Jin Chae et al. JBC 2003), as a template, and using the primers above mentioned. Subsequently, the PCR products were cloned to an expression vector of pGELysRS(2) both at Xba I and Hind III sites, wherein the pGELysRS(2) vector was manufactured by deleting Xba I restriction enzyme at 5' region of ATG-LysRS of an expression vector, pGELysRS, that effectively expresses a protein in soluble type. Thereby, pSim-2-2-zA1A2 expression vector was developed.

In order to prepare another desired protein, which regulates in vivo immune response, using Sim-2 BTM, cytoplasmic domain of CTLA-4 protein, which is a negative regulator during the T cell activation process, was employed as a fusion partner to the Sim-2 BTM. The CTA-4 is a cell membrane protein found on the surface of activated T cell, and it is known to inhibit T cell activation by binding any one of proteins of B7 family on the surface of APC (Antigen Presenting Cell). In order to prepare a fusion protein of Sim-2 BTM and cytoplasmic domain of CTLA-4, an expression vector of pSim-2-CTLA-4 was designed, and its construct was displayed in FIG. 12(b). In order to make this expression vector, a 5' primer of SEQ. ID No.:15 comprising nucleic acid sequence of Xba I restriction enzyme, nucleic acid sequence of Sim-2 BTM and N-terminal nucleic acid sequence of CTLA-4 protein, and a 3' primer of SEQ. ID No.:13 comprising nucleic acid sequence of Hind III and C-terminal nucleic acid sequence of CTLA-4 were prepared. Then, PCR amplification was carried out using primary T cell cDNA mixture synthesized in our laboratory (Wook-Jin Chae et al. JBC 2003), as a template, and using the primers above mentioned. Subsequently, the PCR products were cloned to an expression vector of pGELysRS(2) both at Xba I and Hind III sites, wherein the pGELysRS(2) vector was generated by deleting Xba I restriction enzyme at 5' region of ATG-LysRS of an expression vector, pGELysRS, that effectively expresses a protein in soluble type. Thus, pSim-2-CTLA-4 expression vector was developed.

Figure 13:
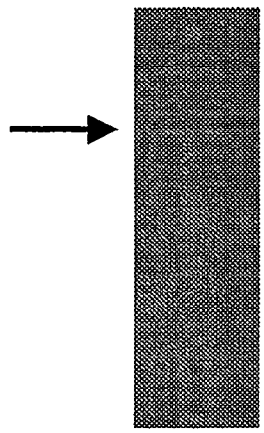
FIG. 13 shows coomassie blue staining of purified fusion proteins of pSim-2-zA1A2(a) and pSim-2-CTLA4(b).
Figure 13:
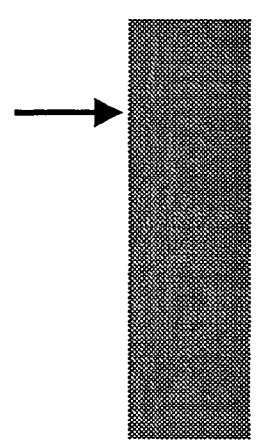

Using the prepared pSim-2-zA1A2 and pSim-2-CTLA-4 expression vectors, E. coli of BL21 (invitrogen, cat.no.: c7010-03) was transformed by heat shock transformation. After isolating and purifying the expressed fusion proteins, the obtained products were subject to SDS-PAGE followed by coomasie blue staining. The FIGS. 13(*a*) and (b) represent the results. With the isolated and purified Sim-2-zA1A2 fusion protein and Sim-2-CTLA-4 fusion protein, immunosuppressive effects in vivo were examined and analyzed using the organ rejection animal models of rat heterocardiac allograft as disclosed in the Example 9 (Jae-Hyuck Sim et al. PNAS vol. 9, no. 16, 10617-10622, 2002). The results are represented in Table 2.

TABLE 2

| Drugs | Concentration (mg/kg) | Administration routes | Days alive | Rat number |
|---|---|---|---|---|
| Cremophor | 5 | I.P. | 9 | 4 |
|  | 5 | I.P. | 10 | 3 |
| CyclosporinA/Cremophor | 5 | I.P. | >100 | 2 |
| Sim-2-zA1A2/PBS | 0.01 | I.P. | >160 | 15 |
| Sim-2-CTLA-4/PBS | 0.04 | I.P. | >160 | 11 |

As the results, the transplanted organs in the organ rejection animal models, which were respectively given Sim-2-zA1A2 and Sim-2-CTLA-4 by IP injection (0.01 ug/ml) or by subcutaneous administration (0.04 ug/ml), operated 160 days or more, while the transplanted organs in the organ rejection animal models, which were given conventional immunosuppressor of CsA (cyclosphorin A) by IP injection, operated 100 days or more. On the other hand, the transplanted organs in the organ rejection animal models, which were given cremophor by IP injection, operated only 9 or 10 days. These results suggested that both of zA1A2 type of TCR z chain and CTLA-4 were efficiently transduced into the T cells by Sim-2 BTM and inhibited T cell activation to represent immunosuppressive effects.

Example 11

Transduction of Macromolecules into Plant Callus Cells Using Sim-2 BTM

Figure 14:
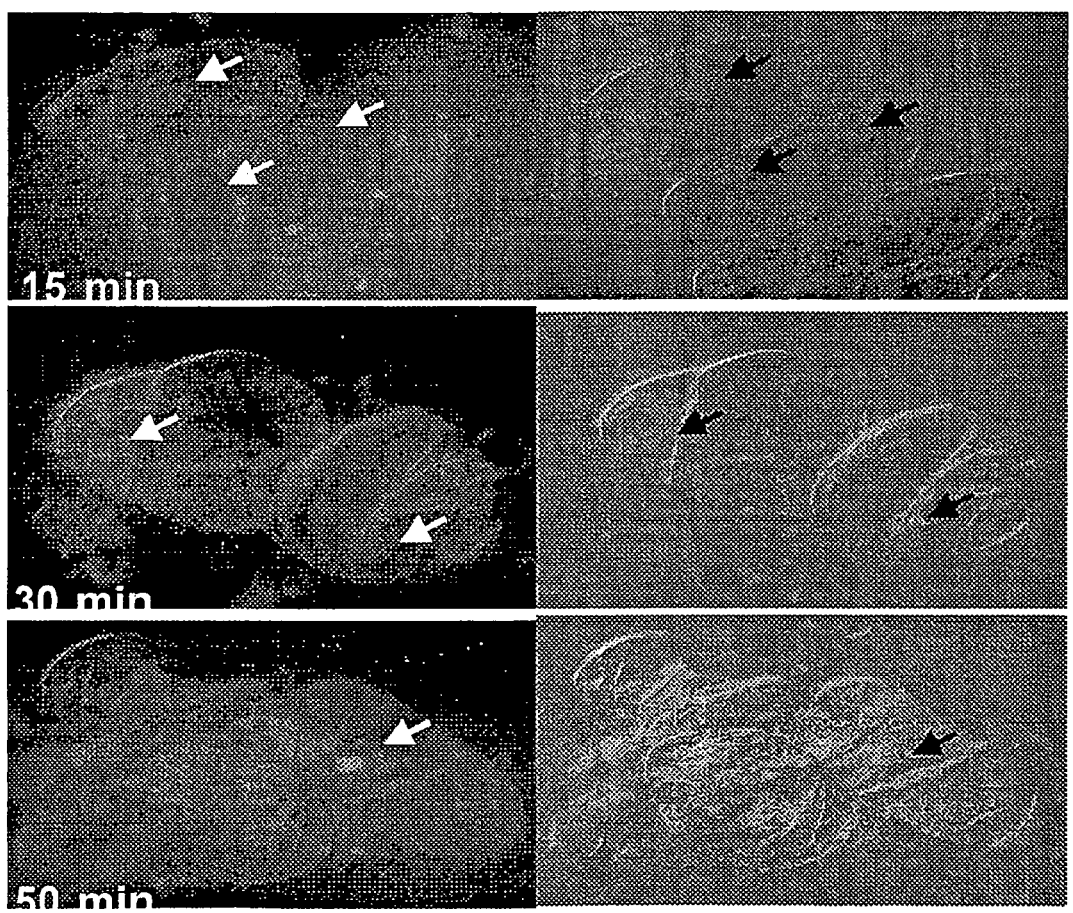
FIG. 14 shows the transmission of β-gal proteins into callus cells using Sim-2-BTM.

The desired proteins were transduced into non-animal cells using Sim-2 BTM in this example. Briefly, cultured plant callus cells were given 10 uM of Sim-2-β-gal fusion proteins, and, after 1 hr, the cells were examined under confocal microscope in order to analyze the transduction level of β-galactosidase into the cells. The results were displayed in FIG. 14. Specifically, collected tobacco leaves were cultured in callus inducing medium including auxin and cytokine, and the produced plant callus was cultured in agar free MS medium (suspension culture). As the results, after 15 min from the introduction of fusion protein using Sim-2 BTM, it was observed that β-galactosidase was effectively transduced not only into the callus cells but also into the nucleus of the cells.

Example 12

Transduction of Macromolecules into Various Kinds of Bacteria by Sim-2 BTM

Figure 15:
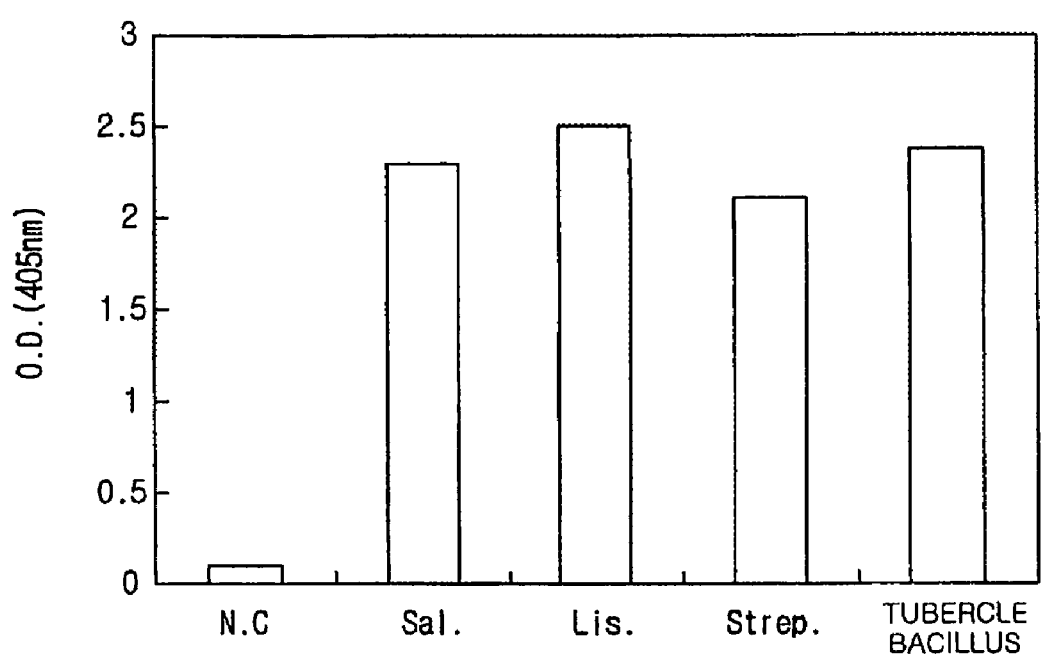
FIG. 15 represents the transduction of β-gal proteins into bacteria, *salmonella, streptococus*, and *tuberculous bacillus* using Sim-2 BTM.

The desired proteins were transduced into various kinds of bacteria in this example. 1 uM of Sim-2-β-gal fusion proteins was introduced to various bacteria, such as *Salmonella typhymirium, Listeria monocytogenesis, Streptococcus aureus* and *tubercle bacillus*. After 1 hr from the introduction, the activities of the transduced β-galactosidase were detected and the results were shown in FIG. 15. As the results, it was confirmed that macromolecules were efficiently transduced into the bacterial cells with Sim-2 BTM.

Example 13

Figure 16:
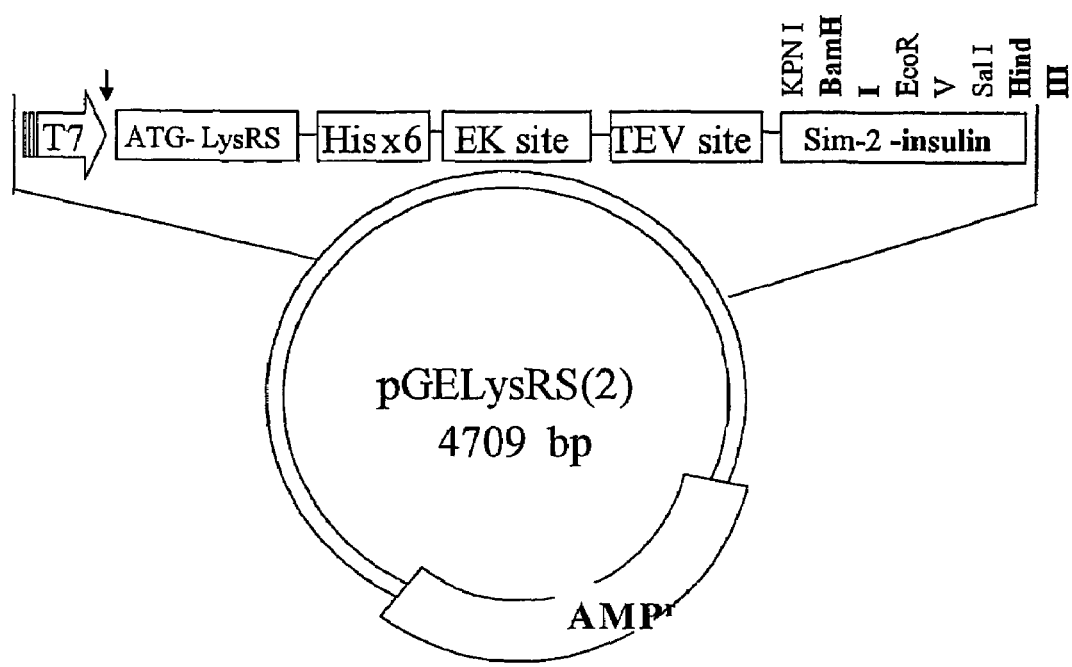
FIG. 16 illustrates the construct of an expression vector of pSim-2-insulin in order to produce fusion protein between Sim-2-BTM and insulin.
Figure 17A:
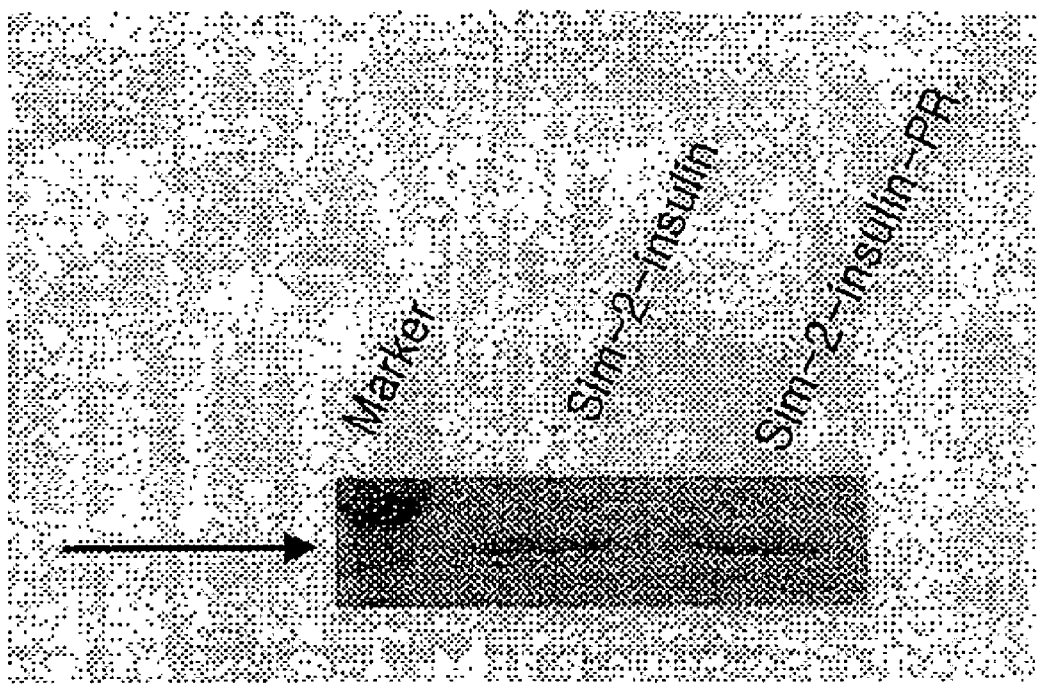
FIG. 17A shows coomassie blue staining of purified fusion protein of pSim-2-insulin and pSim-2-insulin-PR.
Figure 17B:
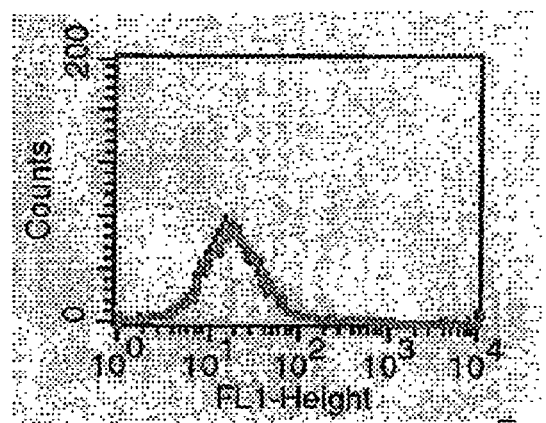
FIG. 17B represents the transduction of fusion protein recombinent insulin pSim-2-insulin and pSim-2-insulin-PR into Jurkat T cells.
Figure 17B:
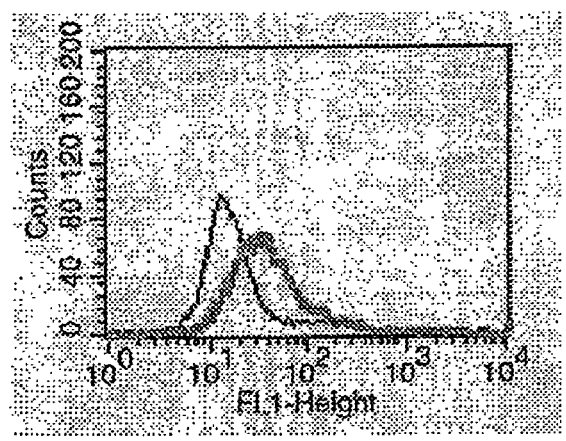
Figure 17B:
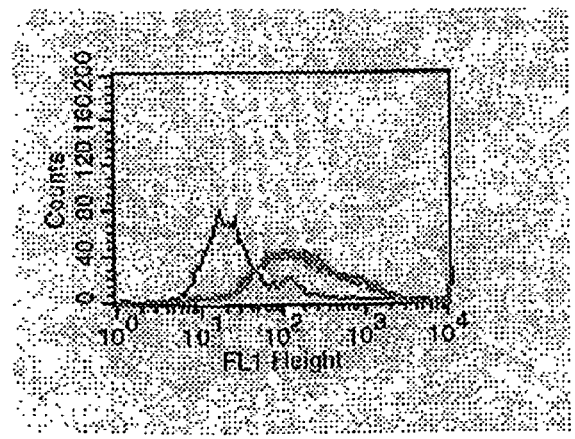

Production of Protein Drugs having Natural Folding Structure and Function Using Sim-2 BTM A fusion protein of Sim-2 BTM and biologically active functional regulatory protein, which was expressed and purified from bacteria, was reformed so as to have natural folding structure and functions. Specifically, the fusion protein isolated and purified from bacteria was transferred again into CHO (Chinese hamster ovary) cells, and then the fusion protein, which had complete folding structure and functions found in natural state, was isolated and purified. As for purified 2 (two) types of fusion proteins, biological activity regulating capabilities were examined. For this examination, an expression vector pSim-2-insulin was designed in order to prepare fusion protein between Sim-2 BTM and human insulin. In order to make this expression vector, a 5' primer of SEQ. ID No.:17 comprising nucleic acid sequence of Xba I restriction enzyme, nucleic acid sequence of Sim-2 BTM and N-terminal nucleic acid sequence of human insulin, and a 3' primer of SEQ. ID No.:18 comprising nucleic acid sequence of Hind m and C-terminal nucleic acid sequence of human insulin were prepared. Then, PCR amplification was carried out using human pancreas beta cells prepared in our laboratory, as a template, and using the primers above mentioned. Subsequently, the PCR products were cloned to an expression vector of pGELysRS(2) both at Xba I and Hind m sites, wherein the pGELysRS(2) vector was generated by deleting Xba I restriction enzyme at 5' region of ATG-LysRS of an expression vector, pGELysRS, that effectively expresses a protein in soluble type. Thus, pSim-2-insulin expression vector was provided and its construct was shown in FIG. 16. With the prepared pSim-2-insulin expression vectors, E. coli of BL21 (invitrogen, cat.no.: c7010-03) was transformed by heat shock transformation. Then, the expressed pSim-2-insulin fusion protein was collected and purified according to the example 2. 1 ug/ml of the purified Sim-2-insulin fusion protein was transferred again into the CHO cells, and then Sim-2-insulin fusion protein, which was considered as to have natural structure and functions, was isolated and purified, and the obtained fusion protein was named as Sim-2-insulin-PR. These 2 (two) types of fusion proteins of Sim-2-insulin and Sim-2-insulin-PR were subject to SDS-PAGE and coomasie blue staining. The results are displayed in FIG. 17A. In order to confirm whether these 2 fusion proteins were effectively transferred into Jurkat T cells with Sim-2 BTM, Jurkat T cells were treated respectively with these 2 fusion proteins and recombinant insulin not fused to Sim-2 BTM, as disclosed in the Example 3. Following the treatment, the transduction level of insulin into the cells was detected using mAb to the insulin and was compared. The results are shown in FIG. 17B. As the results, both of Sim-2-insulin and Sim-2-insulin-PR were transduced efficiently into the Jurkat T cells, while almost none of the recombinant insulins, which did not have Sim-2 BTM, was transduced into the T cells.

Example 14

Lowering Blood Glucose Level Using Sim-2-Insulin Fusion Protein

Blood glucose level lowering was examined using Sim-2-insulin and Sim-2-insulin-PR in the Example 13 with Streptozotocin-Induced diabetic mice. After 3 (three) days of abstinence, STZ (Sigma Chemical Co, St Louis, USA) (60 mg/kg) were given the fusion proteins by IV injection. Insulin dependent diabetic mice were defined having 20 mmol/L or more blood glucose level together with other diabetic syndrome such as polyurea etc. All the in vivo studies were carried out after 2 weeks from the induction of diabetes. Recombinant insulin alone, Sim-2-insulin and Sim-2-insulin-PR in the Example 13 were, respectively, administered to the mice by IP injection (1-10 mM), and the blood glucose levels in the mice were monitored. In order to analyze the level of blood glucose, about 0.2 ml of blood was collected from each of the mice after anesthetizing them, and then the blood was subject to centrifuge at 13,000 rpm for 3 min. Next, about 15 ml of serum was added to 1.5 ml of glucose kit agent (BiosystemSA, Barcelona, Spain) and the mixture was incubated at 37° C. for 10 min in water-bath. The level of blood glucose was detected with blood glucose analyzer (Quik-Lab, Ames, Miles Inc. Elkart, Ind., USA). The results are displayed in Table 3.

TABLE 3

| Drug | Before administration | After administration |
| --- | --- | --- |
| PBS | 5270 | 5390 |
| Recombinant insulin | 5600 | 2320 |
| Sim-2-insulin | 6450 | 1570 |
| Sim-2-insulin-PR | 6630 | 350 |

As shown in Table 3, the recombinant insulin lowered blood glucose level by 50%, and the Sim-2-insulin lowered the level by 70%. On the other hand, the Sim-2-insulin-PR, which was obtained in CHO cells and considered as to have natural protein folding structure and functions, lowered level by 90% or more. As the results, once the fusion protein is transferred into animal cells with Sim-2 BTM, it is considered as to be subject to protein folding machinery in the cells, thereby the protein has natural folding structure and functions. Briefly, after producing numerous desired proteins from bacteria using Sim-2 BTM massively, the obtained recombinant proteins were transferred again with the Sim-2 BTM into the cells, which naturally generate in vivo the same type of proteins as the recombinant proteins, and then the desired proteins were purified from the cell culture. The finally purified desired proteins are expected to have significantly excellent efficacy when using it as a basic and clinical treating agent.

INDUSTRIAL APPLICABILITY

As disclosed above, Sim-2 BTM Sim-2 of the present invention, which includes amino acid sequence of SEQ. ID No.:1, delivers biologically active functional regulatory molecules in vivo and in vitro into the cytosol, organelles or nucleus of prokaryotic and eukaryotic cells, via numerous paths, for example, intramascular, intraperitoneal, intravein, oral, nasal, subcutaneous, intradermal, mucosal, and inhalation. Thus, this invention can be used to provide protein drugs, recombinant vaccines, DNA/RNA vaccines, and functional genes. Furthermore, this invention can be used to provide novel methods for treating disease using protein, genes, chemical compounds. Furthermore, this invention can be used to provide novel drug delivery system and proteins having natural structure and functions.

What is claimed is:

1. A peptide wherein the peptide is a purified peptide consisting of SEQ. ID NO.:1 derived from human transcription factor SIM2 beginning at the 558th marker of human transcription factor SIM2 and ending at the 566th marker of human transcription factor SIM2, wherein the pepride has the biological activity of transducing a biologically active, functional or regulatory molecule into prokaryotic cells or eukcaryotic cells.

2. The peptide of claim 1, wherein the biologically active, functional or regulatory molecule is any one of a protein, a DNA fragment, an RNA fragment, a carbohydrate, a lipid or a chemical compound.

3. The peptide of claim 1, wherein the peptide is fused to a biologically active, functional or regulatory molecule selected from the group consisting of a protein, a DNA fragment, an RNA fragment, a carbohydrate, a lipid and a chemical compound.

4. A recombinant expression vector wherein the vector is a DNA sequence encoding the peptide consisting of SEQ. ID NO.:1 derived from human transcription factor SIM2 beginning at the 558th marker of human transcription factor SIM2 and ending at the 566th marker of human transcription factor SIM2.

5. A method of transducing a biologically active, functional or regulatory molecule into a eukaryotic cell comprising:

preparing a peptide construct wherein the peptide construct is a purified peptide consisting of SEQ. ID NO.:1 derived from human transcription factor SIM2 beginning at the 558th marker of human transcription factor SIM2 and ending at the 566th marker of human transcription factor SIM2 and a biologically active, functional or regulatory molecule; and transducing the peptide construct in vivo to a subject through administration routes consisting of intramuscular, intraperitoneal, intravenous, oral, nasal, subcutaneous, intradermal, mucosal and inhalation routes.

6. A method of transducing a biologically active, functional or regulatory molecule into a prokaryotic or eukaryotic cell comprising:

preparing a peptide construct wherein the peptide construct is a purified peptide consisting of SEQ. ID NO.:1 derived from human transcription factor SIM2 beginning at the 558th marker of human transcription factor SIM2 and ending at the 566th marker of human transcription factor SIM2 and a biologically active, functional or regulatory molecule; and transducing said peptide construct in vitro to said prokaryotic or eukaryotic cell.

* * * * *

SEQUENCE LISTING

```
<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<223> OTHER INFORMATION: Biomolecule transduction motif

<400> SEQUENCE: 1

Ala Lys Ala Ala Arg Gln Ala Ala Arg
 1               5

<210> SEQ ID NO 2
<211> LENGTH: 66
<212> TYPE: DNA
<213> ORGANISM: Artificial Sequence
<220> FEATURE:
<223> OTHER INFORMATION: 5' primer for Sim-2
```

```
<220> FEATURE:
<221> NAME/KEY: misc_feature
<222> LOCATION: (4)..(9)
<223> OTHER INFORMATION: BamHI site

<400> SEQUENCE: 2
cgcggatccg ccaaagccgc ccgccaggcc gcccggtcta gagatcccgt cgttttacaa      60
cgtgac                                                                66

<210> SEQ ID NO 3
<211> LENGTH: 26
<212> TYPE: DNA
<213> ORGANISM: Artificial Sequence
<220> FEATURE:
<223> OTHER INFORMATION: 3' primer for beta-gal
<220> FEATURE:
<221> NAME/KEY: misc_feature
<222> LOCATION: (3)..(8)
<223> OTHER INFORMATION: BglII site

<400> SEQUENCE: 3
gaagatcttt attttgaca ccagac                                           26

<210> SEQ ID NO 4
<211> LENGTH: 75
<212> TYPE: DNA
<213> ORGANISM: Artificial Sequence
<220> FEATURE:
<223> OTHER INFORMATION: 5' primer for tat
<220> FEATURE:
<221> NAME/KEY: misc_feature
<222> LOCATION: (4)..(9)
<223> OTHER INFORMATION: BamHI site

<400> SEQUENCE: 4
cgcggatcct atggaaggaa gaagaagcgg agacaaagac gacgatctag agatcccgtc      60
gttttacaac gtgac                                                      75

<210> SEQ ID NO 5
<211> LENGTH: 18
<212> TYPE: DNA
<213> ORGANISM: Artificial Sequence
<220> FEATURE:
<223> OTHER INFORMATION: 3' primer for eGFP
<220> FEATURE:
<221> NAME/KEY: misc_feature
<222> LOCATION: (4)..(8)
<223> OTHER INFORMATION: BglII site

<400> SEQUENCE: 5
gaagatcttt tacttgta                                                   18

<210> SEQ ID NO 6
<211> LENGTH: 18
<212> TYPE: DNA
<213> ORGANISM: Artificial Sequence
<220> FEATURE:
<223> OTHER INFORMATION: 5' primer for B7.1
<220> FEATURE:
<221> NAME/KEY: misc_feature
<222> LOCATION: (4)..(9)
<223> OTHER INFORMATION: BamHI site

<400> SEQUENCE: 6
cgcggatccg gccacaca                                                   18

<210> SEQ ID NO 7
```

```
<211> LENGTH: 18
<212> TYPE: DNA
<213> ORGANISM: Artificial Sequence
<220> FEATURE:
<223> OTHER INFORMATION: 3' primer for B7.1
<220> FEATURE:
<221> NAME/KEY: misc_feature
<222> LOCATION: (3)..(8)
<223> OTHER INFORMATION: BglII site

<400> SEQUENCE: 7
gaagatcttt acagggcg                                               18

<210> SEQ ID NO 8
<211> LENGTH: 21
<212> TYPE: DNA
<213> ORGANISM: Artificial Sequence
<220> FEATURE:
<223> OTHER INFORMATION: 5' primer for Gal4
<220> FEATURE:
<221> NAME/KEY: misc_feature
<222> LOCATION: (4)..(9)
<223> OTHER INFORMATION: XbaI site

<400> SEQUENCE: 8
cgctctagaa agctactgtc t                                           21

<210> SEQ ID NO 9
<211> LENGTH: 21
<212> TYPE: DNA
<213> ORGANISM: Artificial Sequence
<220> FEATURE:
<223> OTHER INFORMATION: 3' primer for Gal4
<220> FEATURE:
<221> NAME/KEY: misc_feature
<222> LOCATION: (4)..(9)
<223> OTHER INFORMATION: HindIII site

<400> SEQUENCE: 9
cccaagcttc ggcgatacag t                                           21

<210> SEQ ID NO 10
<211> LENGTH: 119
<212> TYPE: DNA
<213> ORGANISM: Artificial Sequence
<220> FEATURE:
<223> OTHER INFORMATION: Gal4 binding sequence

<400> SEQUENCE: 10
ctcgaggaca gtactccgct cggaggacag tactccgatc cgtcgactct agagggtata     60
taatgcgcca gctcgaattc atcagcttgg cgagattttc aggagctaag gaagctaaa    119

<210> SEQ ID NO 11
<211> LENGTH: 45
<212> TYPE: DNA
<213> ORGANISM: Artificial Sequence
<220> FEATURE:
<223> OTHER INFORMATION: N terminal of BamhI-Sim-2-B7
<220> FEATURE:
<221> NAME/KEY: misc_feature
<222> LOCATION: (4)..(9)
<223> OTHER INFORMATION: BamHI site

<400> SEQUENCE: 11
cgcggatccg ccaaagccgc cgccaggcc gcccggggcc acaca                   45

<210> SEQ ID NO 12
<211> LENGTH: 18
```

```
<212> TYPE: DNA
<213> ORGANISM: Artificial Sequence
<220> FEATURE:
<223> OTHER INFORMATION: C terminal of BgIII and B7
<220> FEATURE:
<221> NAME/KEY: misc_feature
<222> LOCATION: (3)..(8)
<223> OTHER INFORMATION: Bg1II site

<400> SEQUENCE: 12
gaagatcttt acagggcg                                                    18

<210> SEQ ID NO 13
<211> LENGTH: 81
<212> TYPE: DNA
<213> ORGANISM: Artificial Sequence
<220> FEATURE:
<223> OTHER INFORMATION: 5' primer for Sim2-A1A2
<220> FEATURE:
<221> NAME/KEY: misc_feature
<222> LOCATION: (4)..(9)
<223> OTHER INFORMATION: BamHI site

<400> SEQUENCE: 13
cgcggatccg ccaaagccgc ccgccaggcc gcccgggggt ctagattcct gagagtgaag      60
ttcagcagga gcgcagagcc c                                                81

<210> SEQ ID NO 14
<211> LENGTH: 72
<212> TYPE: DNA
<213> ORGANISM: Artificial Sequence
<220> FEATURE:
<223> OTHER INFORMATION: 3' primer for Sim-2-A1A2
<220> FEATURE:
<221> NAME/KEY: misc_feature
<222> LOCATION: (4)..(9)
<223> OTHER INFORMATION: Bg1II site

<400> SEQUENCE: 14
cccaagcttc ttgtcatagt cgtccttgta gtcgcggccg ccgcgagggg gcagggcctg      60
catgtgaagg gc                                                          72

<210> SEQ ID NO 15
<211> LENGTH: 69
<212> TYPE: DNA
<213> ORGANISM: Artificial Sequence
<220> FEATURE:
<223> OTHER INFORMATION: 5' primer for Sim-2-CTLA4
<220> FEATURE:
<221> NAME/KEY: misc_feature
<222> LOCATION: (4)..(9)
<223> OTHER INFORMATION: BamHI site

<400> SEQUENCE: 15
cgcggatccg ccaaagccgc ccgccaggcc gcccggggt ctagaaaaat gctaaagaaa       60
agaagccct                                                              69

<210> SEQ ID NO 16
<211> LENGTH: 72
<212> TYPE: DNA
<213> ORGANISM: Artificial Sequence
<220> FEATURE:
<223> OTHER INFORMATION: 3' primer for Sim-2-CTLA4
<220> FEATURE:
<221> NAME/KEY: misc_feature
<222> LOCATION: (4)..(9)
<223> OTHER INFORMATION: Bg1II site
```

```
-continued

<400> SEQUENCE: 16
cccaagcttc ttgtcatagt cgtccttgta gtcgcggccg ccattgatgg gaataaaata     60
aggctgaaat tg                                                         72

<210> SEQ ID NO 17
<211> LENGTH: 67
<212> TYPE: DNA
<213> ORGANISM: Artificial Sequence
<220> FEATURE:
<223> OTHER INFORMATION: 5' primer for Sim-2-insulin
<220> FEATURE:
<221> NAME/KEY: misc_feature
<222> LOCATION: (4)..(9)
<223> OTHER INFORMATION: BamHI site

<400> SEQUENCE: 17
cgcggatccg ccaaagccgc ccgccaggcc gcccggggggc agggttccag ggtggctgga    60
ccccagg                                                               67

<210> SEQ ID NO 18
<211> LENGTH: 77
<212> TYPE: DNA
<213> ORGANISM: Artificial Sequence
<220> FEATURE:
<223> OTHER INFORMATION: 3' primer for Sim-2-insulin
<220> FEATURE:
<221> NAME/KEY: misc_feature
<222> LOCATION: (4)..(9)
<223> OTHER INFORMATION: BglII site

<400> SEQUENCE: 18
cccaagcttc ttgtcatagt cgtccttgta gtcgcggccg cgctggttca agggctttat     60
tccatctctc tcggtgc                                                    77
```